United States Patent
Gayda et al.

(10) Patent No.: US 9,005,901 B2
(45) Date of Patent: Apr. 14, 2015

(54) ASSAY WITH INTERNAL CALIBRATION

(71) Applicant: Abbott Laboratories, Abbott Park, IL (US)

(72) Inventors: Susan Gayda, Gurnee, IL (US);
Qiaoqiao Ruan, Kildeer, IL (US);
Joseph P. Skinner, Lake Villa, IL (US);
Sergey Y. Tetin, Lindenhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/833,365

(22) Filed: Mar. 15, 2013

(65) Prior Publication Data

US 2014/0273272 A1  Sep. 18, 2014

(51) Int. Cl.
G01N 33/53 (2006.01)
G01N 35/00 (2006.01)
G01N 33/543 (2006.01)

(52) U.S. Cl.
CPC .... *G01N 35/00693* (2013.01); *G01N 33/54306* (2013.01)

(58) Field of Classification Search
None
See application file for complete search history.

(56) References Cited

U.S. PATENT DOCUMENTS

| | | | |
|---|---|---|---|
| 4,595,661 A | 6/1986 | Cragle et al. |
| 5,006,309 A | 4/1991 | Khalil et al. |
| 5,063,081 A | 11/1991 | Cozzette et al. |
| 5,089,424 A | 2/1992 | Khalil et al. |
| 5,242,828 A | 9/1993 | Bergstrom et al. |
| 5,260,203 A | 11/1993 | Ladner et al. |
| 5,294,404 A | 3/1994 | Grandone et al. |
| 5,352,803 A | 10/1994 | Mattingly |
| 5,359,093 A | 10/1994 | Adamczyk et al. |
| 5,496,925 A | 3/1996 | Mattingly |
| 5,573,904 A | 11/1996 | Mattingly |
| 5,593,896 A | 1/1997 | Adamczyk et al. |
| 5,770,380 A | 6/1998 | Hamilton et al. |
| 6,184,042 B1 | 2/2001 | Neumann |
| 6,225,047 B1 | 5/2001 | Hutchens et al. |
| 6,329,209 B1 | 12/2001 | Wagner et al. |
| 6,350,579 B1 | 2/2002 | Nelson |
| 6,818,418 B1 | 11/2004 | Lipovsek et al. |
| 7,115,396 B2 | 10/2006 | Lipovsek et al. |
| 8,192,943 B2 | 6/2012 | Harris et al. |
| 2003/0148542 A1 | 8/2003 | Pawlak et al. |
| 2003/0170881 A1 | 9/2003 | Davis et al. |
| 2004/0018577 A1 | 1/2004 | Emerson Campbell et al. |
| 2004/0029177 A1 | 2/2004 | Nadaoka et al. |
| 2004/0175756 A1 | 9/2004 | Kolkman et al. |
| 2005/0048512 A1 | 3/2005 | Kolkman et al. |
| 2005/0053973 A1 | 3/2005 | Kolkman et al. |
| 2005/0054078 A1 | 3/2005 | Miller et al. |
| 2005/0089932 A1 | 4/2005 | Kolkman et al. |
| 2005/0221384 A1 | 10/2005 | Kolkman et al. |
| 2006/0160164 A1 | 7/2006 | Miller et al. |
| 2009/0269777 A1 | 10/2009 | Birkenmeyer et al. |
| 2010/0167301 A1 | 7/2010 | Collier et al. |
| 2011/0117674 A1 | 5/2011 | Melin et al. |
| 2012/0308997 A1 | 12/2012 | Ruan et al. |
| 2014/0273035 A1 | 9/2014 | Dowell et al. |

FOREIGN PATENT DOCUMENTS

| | | |
|---|---|---|
| EP | 0 916 951 B1 | 1/2003 |
| EP | 1 361 435 A1 | 11/2003 |
| EP | 2 405 019 A1 | 1/2012 |
| WO | WO 89/11101 | 11/1989 |
| WO | WO 91/19196 | 12/1991 |
| WO | WO 95/17675 | 6/1995 |
| WO | WO 98/39657 | 9/1998 |
| WO | 99/51773 | 10/1999 |
| WO | 00/56934 | 9/2000 |
| WO | 2007089564 | 8/2007 |
| WO | WO 2009/126336 | 10/2009 |
| WO | WO 2011/097552 | 8/2011 |
| WO | WO 2012/142242 | 10/2012 |
| WO | WO2012170428 | 12/2012 |
| WO | WO 2013/088429 | 6/2013 |
| WO | WO 2014/143323 | 9/2014 |
| WO | WO 2014/149111 | 9/2014 |

OTHER PUBLICATIONS

Adamczyk M., et al., "Chemiluminescence Quenching of Pteroic Acid-N-sulfonyl-acridinium-9-carboxamide Conjugates by Folate Binding Protein," Bioorganic and Medicinal Chemistry Letters 14 (2004), pp. 2313-2317.

Adamczyk M., et al., "Chemiluminescent Acridinium-9-Carboxamide Boronic Acid Probes: Application to a Homogeneous Glycated Hemoglobin Assay," Bioorganic & Medicinal Chemistry Letters 16 (2006), pp. 1324-1328.

Adamczyk M., et al., "Intrinsic Factor-Mediated Modulation of Cyanocobalamin-N-sulfonyl-acridinium-9-carboxamide Chemiluminescence," Bioorganic and Medicinal Chemistry Letters 14 (2004), pp. 3917-3921.

Adamczyk M., et al., "Regiodependent Luminescence Quenching of Biotinylated N-Sulfonyl-acridinium-9-carboxamides by Avidin ," Organic Letters, 2003, vol. 5 (21), pp. 3779-3782.

Beste G., et al., "Small Antibody-Like Proteins with Prescribed Ligand Specificities Derived from the Lipocalin Fold," Proceedings of the National Academy of Sciences, 1999, vol. 96 (5), pp. 1898-1903.

Ku et al., Alternate Protein Frameworks for Molecular Recognition: Proc. Natl. Acad. Sci. USA, vol. 92, pp. 6552-6556 (1995).

Murali et al., "Antibody Like Peptidomimetics As Large Scale Immunodetection Probes" Cell. Mol. Biol. vol. 49 (2), pp. 209-216 (2003) Medline Abstract only.

Olejniczak, E.T., et al., "Rapid Determination of Antigenic Epitopes in Human NGAL Using NMR" Biopolymers, vol. 93 (7) pp. 657-667 (2010).

Polak, "Introduction to Immunocytochemistry," 2nd Edition, 1977, pp. 5-10.

(Continued)

*Primary Examiner* — Jacob Cheu
(74) *Attorney, Agent, or Firm* — Audrey L. Bartnicki; Jennifer Wahlsten; Emily M. Haliday

(57) ABSTRACT

Provided herein are kits and methods for assays with internal calibration.

17 Claims, 4 Drawing Sheets

(56) References Cited

OTHER PUBLICATIONS

Polak J.M., et al., Introduction to Immunocytochemistry, 2nd Edition, Springer-Verlag, 1997, Table of Contents.
Silverman et al. "Multivalent Avimer Proteins Evolved by Exon Shuffling of a Family of Human Receptor Domains" Nature Biotechnology, vol. 23 (12) pp. 1556-1561 (2005).
PCT International Search Report and Written Opinion dated Jun. 4, 2014 issued in PCT/US2013/077063.
PCT International Search Report and Written Opinion dated Mar. 6, 2014 issued in PCT/US2013/077073.
Fernando, et al. (1992) "Studies of the low dose 'hook' effect in a competitive homogeneous immunoassay," *Journal of Immunological Methods* 151(1-2):27-46.
Fernando, et al. (1992) "Studies of the 'hook' effect in the one-step sandwich homogeneous immunoassay" *Journal of Immunological Methods* 151(1-2):47-66.
Frengen, et al. (1995) "A sequential binding assay with a working range extending beyond seven orders of magnitude," *Journal of Immunological Methods* 178(1):131-40.
Kartalov, et al. (2008) "Internally calibrated quantification of protein analytes in human serum by fluorescence immunoassays in disposable elastomeric microfluidic devices," *Electrophoresis* 29(24):5010-5016.
Lindmo, et al. (1990) "Immunometric assay by flow cytometry using mixtures of two particle types of different affinity," *Journal of Immunological Methods* 126(2):183-189.
Ohmura, et al. (2003) "Combinational use of antibody affinities in an immunoassay for extension of dynamic range and detection of multiple analytes," *Analytical Chemistry* 75(1):104-110.

ASSAY WITH INTERNAL CALIBRATION

FIELD

Provided herein are kits and methods for assays with internal calibration.

BACKGROUND

For the past several decades, assays have been performed using fluorescence, chemiluminescence, or other means of generating a signal in response to an analyte. Currently, many assays are performed by measurement of the intensity of a light signal generated in the total volume of a reaction mixture. The light signal generated can be measured by an optical means, wherein the light signal generated is emitted by a large number of molecules. In a typical embodiment, these assays can be carried out by combining a sample suspected of containing an antigen with a reagent comprising a first antibody attached to a solid support, e.g., a microparticle, to form a reaction mixture. The antigen, if present in the sample, specifically binds to the first antibody. A conjugate, which comprises a second antibody having a label attached thereto, is introduced to the reaction mixture and specifically binds to the antigen, which is specifically bound to the first antibody, which, as stated previously, is attached to the solid support. Such an assay is referred to as a sandwich assay or an immunometric assay. This type of assay is shown schematically in FIG. 1. The signal attributable to the label is then measured after unbound conjugate is removed from the reaction mixture, typically by performing a wash step. The signal that is derived from the total volume of the reaction mixture is measured and then compared to a calibration curve to establish the concentration of antigen present in the sample.

When the assay does not includes a separation of bound from unbound sample analyte it is considered 'one-step' assay. When the assay does include a separation of bound from unbound sample analyte it generally is considered a 'two-step assay' (or delayed one-step assay, depending on how the separation is carried out).

In a standard sandwich assay, the first step is to generate a calibration curve using a set of analyte calibrators with known concentrations. Then, the concentration of an unknown sample is determined using the calibration curve.

SUMMARY

Provided are kits and methods for the internal calibration of an assay, e.g., an immunoassay. The internal calibration methods and kits provided herein eliminate the need to prepare a calibration curve and allow for the determination of analyte presence and/or concentration of numerous test samples based on a single internally calibrated reference point.

Accordingly, in one aspect, kits are provided. In some embodiments, the kits comprise: a tracer analyte comprising a first label, a capture analyte-binding molecule, and a detection analyte-binding molecule comprising a second label, wherein the capture analyte-binding molecule and the detection analyte-binding molecule can concurrently bind to the tracer analyte. In varying embodiments, the capture analyte-binding molecule is attached to a solid support. In some embodiments, the solid support is selected from the group consisting of a particle, a microparticle, a bead, an electrode and a multiwell plate. In some embodiments, one or both of the capture analyte-binding molecule and/or the detection analyte-binding molecule is an antibody or fragment thereof. In some embodiments, one or both of the first label and the second label is a chromophore. In some embodiments, one or both of the first label and the second label is a fluorophore.

In a further aspect, methods of internally calibrating an assay are provided. In some embodiments, the assays comprise:

a) contacting a capture analyte-binding molecule with a predetermined concentration of tracer analyte labeled with a first label and a predetermined concentration of detection analyte-binding molecule labeled with a second label, wherein the capture analyte-binding molecule and the detection analyte-binding molecule concurrently bind to the tracer analyte;

b) measuring the signal intensities obtained of the first label ($I_1^o$) and of the second label ($I_2^o$);

c) determining a correction factor (F) as the ratio of the intensity of the second label ($I_2^o$) to the intensity of the first label ($I_1^o$); whereby the determination of the correction factor allows for the internal calibration of the assay. Generally, this method is performed in the absence of a test sample.

In a further aspect, methods of determining the concentration of analyte in one or more test samples are provided. In some embodiments, the methods comprise:

a) contacting a capture analyte-binding molecule with a predetermined concentration of tracer analyte labeled with a first label and a predetermined concentration of detection analyte-binding molecule labeled with a second label in either the absence or presence of one or more test samples that may comprise test analyte, wherein the capture analyte-binding molecule and the detection analyte-binding molecule concurrently bind to the tracer analyte and, if present, to test analyte in said one or more test samples;

b) measuring the signal intensities obtained in the absence of said one or more test samples of the first label ($I_1^o$) and the second label ($I_2^o$);

c) determining a correction factor (F) as the ratio of the intensity of the second label ($I_2^o$) to the intensity of the first label ($I_1^o$);

d) measuring the signal intensities obtained in the presence of said one or more test samples of the first label ($I_1$) and the second label ($I_2$); and e) determining the concentration of test analyte in said one or more test samples by dividing the ratio of the intensity of the second label ($I_2$) to the intensity of the first label ($I_1$) by the correction factor (F) and subtracting the predetermined concentration of tracer analyte. In varying embodiments, steps b) and d) can be done at the same time, or in any order. In some embodiments, steps d) and e) are repeated one or more times. In some embodiments, steps a) through c) are performed only once. In some embodiments, the predetermined concentration of tracer analyte ranges from less than the expected test analyte concentration to about 5-fold higher than the expected targeted test analyte concentration.

With respect to further embodiments of the methods of internally calibrating and the methods of determining a concentration of analyte, in some embodiments the predetermined concentration of tracer analyte is below saturation of the binding capacity of the capture analyte-binding molecule. In some embodiments, a two-step assay format is used. In some embodiments, a one-step assay format is used. In varying embodiments, when a two-step assay format is used, the predetermined concentration of detection analyte-binding molecule equals or exceeds the concentration of analyte and tracer analyte captured in the first step. In varying embodiments, when a one-step assay format is used, the concentration of detection analyte-binding molecule exceeds the concentration of analyte and tracer analyte. In some embodiments, the method is performed using an automated or semi-automated system. In some embodiments, the capture analyte-binding molecule is attached to a solid support. In some embodiments, the solid support is selected from the group consisting of a particle, a microparticle, a bead, an electrode and a multiwell plate. In some embodiments, one or both of the capture analyte-binding molecule and/or the detection analyte-binding molecule is an antibody or fragment thereof. In some embodiment, the first label is a first chromophore and the second label is a second chromophore. In some embodiments, the first label is a first fluorophore and the second label is a second fluorophore.

DETAILED DESCRIPTION

The present disclosure is predicated, in part, on the discovery and design of assays and methods that use an internal calibrator that can correct variations in assay conditions and improve assay precision. Moreover, by replacing the calibrator set with a single calibrator, the number of calibration runs can be reduced, e.g., one calibration run can establish accurate parameters for measuring analyte concentration of numerous sequentially run test samples.

Definitions

The following terms are relevant to the present disclosure:

An "assay" is a biochemical test that measures the presence or concentration of a substance in solutions that frequently contain a complex mixture of substances. Analytes in biological liquids such as serum or urine are frequently assayed using assay methods. Such assays are based on the unique ability of an analyte-binding molecule (e.g., antibody or antigenically reactive fragment thereof) to bind with high specificity to one or a very limited group of molecules. A molecule that binds to an analyte-binding molecule (e.g., antibody or antigenically reactive fragment thereof) is called an analyte or antigen. Assays requiring a separation step, often called separation assays or heterogeneous assays, are popular because they are easy to design, but they frequently require multiple steps including careful washing of a surface onto which the labeled reagent has bound. Some assays can be run without a separation step. Such assays can frequently be carried out simply by mixing the reagents and sample and making a physical measurement. Such assays are called homogeneous assays, or, less frequently, non-separation assays.

Figure 1:
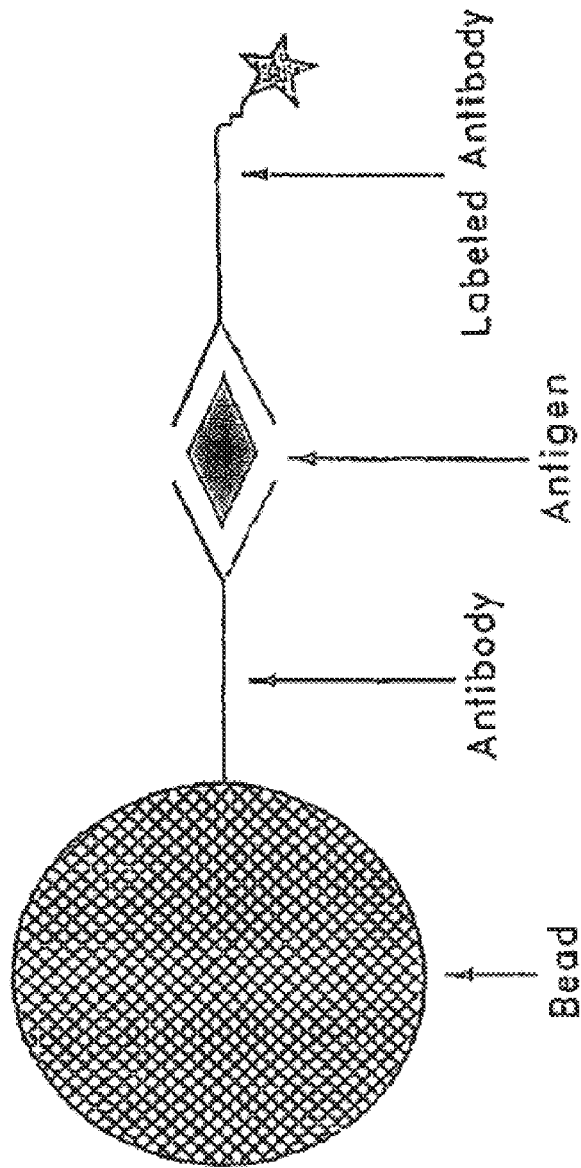
FIG. 1 provides a schematic of a sandwich assay.
Figure 2:
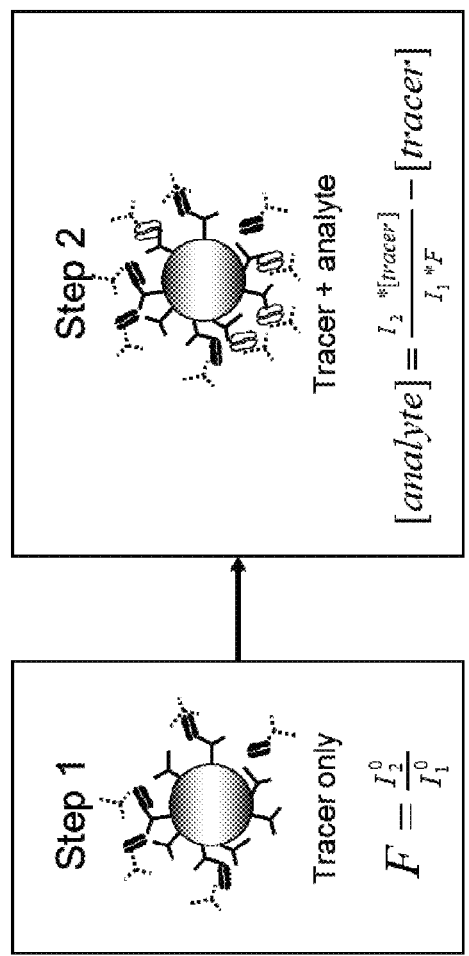
FIG. 2 provides a schematic illustrating an embodiment for performing an assay that is internally calibrated using a single tracer analyte.

As used herein, the expression "sandwich assay" means an assay that employs two analyte-binding molecules that concurrently (e.g., in the same or separate steps) bind to the same analyte. One of the analyte-binding molecules is attached, directly or indirectly, to a solid support, allowing the analyte to be attached directly or indirectly to the solid support, such as, for example, a microparticle or an electrode. The other analyte-binding molecule is attached, directly or indirectly, to a label, allowing the analyte to be attached directly or indirectly to the label to provide a signal for detecting the analyte. For example, one of the analyte-binding molecules can be a capture analyte-binding molecule (e.g., antibody or antigenically reactive fragment thereof) for specifically binding to an analyte (e.g., antigen) in a sample, whereby the analyte (e.g., antigen) is attached directly or indirectly to a solid support, such as, for example, an electrode or a microparticle, and the other analyte-binding molecule can be a detection analyte-binding molecule (e.g., antibody or antigenically reactive fragment thereof) for specifically binding to the analyte (e.g., antigen) in the sample, whereby the analyte (e.g., antigen) is attached directly or indirectly to a label for detecting the antigen. If a relatively high amount of analyte is present in the sample, a higher signal will be produced. If a relatively low amount of analyte is present in the sample, a lower signal will be produced. FIG. 1 is a schematic diagram illustrating a representative example of a sandwich assay.

As used herein, the term "complex" means at least two molecules that are specifically bound to one another. Examples of complexes include, but are not limited to, an analyte bound to an analyte-binding molecule, an analyte bound to a plurality of analyte-binding molecules, e.g., an analyte bound to two analyte-binding molecules, an analyte-binding molecule bound to a plurality of analytes, e.g., an analyte-binding molecule bound to two analytes.

As used herein, the expression "solid support" means any solid surface to which an analyte-binding molecule (e.g., antibody or antigenically reactive fragment thereof) can be attached such that the analyte-binding molecule cannot break free from the solid support in a liquid medium. A solid support can easily be separated from a liquid which the solid support contacts. In varying embodiments, the solid support can be, for example, plastic, derivatized plastic, magnetic or non-magnetic metal, glass or silicon. Representative examples of solid supports, include without limitation, electrodes, test tubes, beads, microparticles, nanoparticles, wells of micro- or multi-well plates, gels, colloids, biological cells, sheet, chip, and other configurations known to those of ordinary skill in the art. An example of an item to which an analyte-binding molecule (e.g., antibody or antigenically reactive fragment thereof) can be attached is a microparticle, such as, for example, a magnetic microparticle. Microparticles typically have an average diameter of less than 1000 microns. The microparticle can easily be separated from a liquid in which it is dispersed. The microparticle is readily dispersed in an aqueous medium. Moreover, optionally the solid support provides a means of recovery of the analyte-binding protein—i.e., means of release or detachment of the analyte-binding molecule from the surface under controlled conditions distinct from those in which the assay is conducted. For example, the analyte-binding molecule may be attached to the solid support by means of a cleavable linker.

As used herein, the expression "capture analyte-binding molecule" means an analyte-binding molecule (e.g., antibody or antigenically reactive fragment thereof) that binds an analyte, e.g., an antigen, to a solid support, with the result that the antibody attaches the analyte to the solid support, whereby the analyte is attached to the solid support either directly or indirectly through an intervening moiety.

As used herein the expression "detection analyte-binding molecule" means an analyte-binding molecule (e.g., antibody or antigenically reactive fragment thereof) that is attached to a moiety that provides or can be made to provide a detectable signal in a chemical or biological reaction.

The term "one-step" assay refers to an assay that does not includes a separation of bound from unbound sample analyte.

The term "two-step" assay refers to an assay that includes a separation of bound from unbound sample analyte.

"About" refers to approximately a +/−10% variation from the stated value. It is to be understood that such a variation is always included in any given value provided herein, whether or not specific reference is made to it.

"Analyte," as further described herein, means a compound or composition to be measured, which may be a ligand, which is monoepitopic or polyepitopic, antigenic or haptenic, a single or plurality of compounds which share at least one common epitopic site or a receptor. Illustrative analytes of interest include without limitation, e.g., proteins, glycoproteins, peptides, polypeptides, oligonucleotides or polynucleotides generally, as well as more specifically, e.g., antibodies, antigens, haptens, hormones, drugs, enzymes, or receptors.

"Antibody" and "antibodies" refer to monoclonal antibodies, multispecific antibodies, bifunctional antibodies, human antibodies, humanized antibodies (fully or partially humanized), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11): 1290-1297 (2007), and International Patent Application Publication No. WO 2001/058956, the contents of each of which are herein incorporated by reference), and functionally active epitope-binding fragments of any of the above. In particular, antibodies include immunoglobulin molecules and immunologically reactive fragments of immunoglobulin molecules, namely, molecules that contain an analyte-binding site. Immunoglobulin molecules can be of any type (for example, IgG, IgE, IgM, IgD, IgA and IgY), class (for example, IgG1, IgG2, IgG3, IgG4, IgA1 and IgA2) or subclass. For simplicity sake, an antibody against an analyte is frequently referred to herein as being either an "anti-analyte antibody," or merely an "analyte antibody". The term "bifunctional antibody," as used herein, refers to an antibody that comprises a first arm having a specificity for one antigenic site and a second arm having a specificity for a different antigenic site, i.e., the bifunctional antibodies have a dual specificity.

"Antibody fragment" and "antibody fragments" refer to a portion of an intact antibody comprising the antigen-binding site or variable region. The portion does not include the constant heavy chain domains (i.e., CH2, CH3 or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Binding Constants" are as described herein. The term "association rate constant," "$k_{on}$" or "$k_a$" as used interchangeably herein, refers to the value indicating the binding rate of a first member of a specific binding pair (SBP1; e.g., an analyte-binding molecule, an antibody (Ab) or analyte reactive fragment thereof) and a second member of a specific binding pair (SBP2; e.g., an analyte (e.g., antigen (Ag)) or the rate of complex formation between the first member of the specific binding pair and the second member of the specific binding pair as shown by the equations below:

$$SBP1 + SBP2 \rightarrow SBP1\text{-}SBP2$$

$$Ab + Ag \rightarrow Ab\text{-}Ag.$$

The term "dissociation rate constant," "$k_{off}$" or "$k_d$" as used interchangeably herein, refers to the value indicating the dissociation rate of SBP1 (e.g., an analyte-binding molecule, an Ab or analyte-reactive fragment thereof) from SBP2 (e.g., Ag) or separation of SBP1-SBP2 complex (e.g., Ab-Ag complex) over time into free SBP1 (e.g., an analyte-binding molecule, an Ab or analyte-reactive fragment thereof) and SBP2 (e.g., Ag) as shown by the equation below:

$$SBP1 + SBP2 \leftarrow SBP1\text{-}SBP2$$

$$Ab + Ag \leftarrow Ab\text{-}Ag.$$

Methods for determining association and dissociation rate constants are well-known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) also can be used.

The term "equilibrium dissociation constant" or "KD" as used interchangeably herein, refers to the value obtained by dividing the dissociation rate ($k_{off}$) by the association rate ($k_{on}$). The association rate, the dissociation rate and the equilibrium dissociation constant are used to represent the binding affinity of an analyte-binding molecule (e.g., antibody or analyte-reactive fragment thereof) to an antigen. This can be described by the following reaction and equation:

$$A + B \rightarrow AB$$

$$K_D = \frac{[AB]}{[A][B]}.$$

Any one of these binding constants, i.e., $k_a$, $k_d$ or $K_D$, conceivably can be employed to assess or compare "binding affinity", i.e., the tendency or strength of binding. However, generally as described herein, binding affinity refers to $K_D$.

"CDR" is used herein to refer to a "complementarity determining region" within an analyte-binding molecule or antibody variable sequence. In antibodies, are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact analyte (e.g., antigen) binding. The methods used herein may utilize CDRs defined according to any of these systems, although certain embodiments use Kabat- or Chothia-defined CDRs.

"Component," "components," and "at least one component," refer generally to a capture antibody, a detection or conjugate antibody, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient serum sample, in accordance with the methods described herein and other methods known in the art. Some components can be in solution or lyophilized for reconstitution for use in an assay.

As used herein, the term "conjugate" means an entity comprising a binding pair member and a label.

"Control" refers to a composition known to not contain analyte ("negative control"), or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

"Correction factor" or "F", used interchangeably herein, refers to a numerical value by which the value describing the signal generated by the label from the detection antigen binding molecule is corrected in an arithmetic operation. In particular, the signal intensities obtained in the absence of test sample are measured for the first label ($I1_0$) and the second label ($I2_0$), and the correction factor (F) is determined as the ratio of the intensity of the second label ($I2_0$) to the intensity of the first label ($I1_0$).

"Epitope," "epitopes," or "epitopes of interest" refer to a site(s) on any analyte that is recognized and can bind to a complementary site(s) on its specific binding partner (e.g., analyte-binding molecule, e.g., antibody or fragment thereof). The analyte and antigen-binding molecule are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an analyte-binding molecule (e.g., antibody or analyte-reactive fragment thereof).

As used herein, the term "intensity" means the amount or degree of strength of electricity, light, heat, or sound per unit area or volume. In varying embodiments, the term "intensity" refers to the number of photons counted per unit of area per unit of time. For example, 1000 photons per unit area may be recorded as 500 counts in a single pixel, while 80 photons per unit area are recorded as 40 counts in a single pixel. The particular conversion depends on the camera system used. Intensity is proportional to the number of photons counted.

"Label" and "detectable label" mean a moiety attached, directly or indirectly, to an analyte-binding molecule (e.g., antibody or analyte-reactive fragment thereof) or an analyte to render the reaction between the analyte-binding molecule (e.g., antibody or analyte-reactive fragment thereof) and the analyte detectable, and the an analyte-binding molecule (e.g., antibody or analyte-reactive fragment thereof) or analyte so labeled is referred to as "detectably-labeled." A label can produce a signal that is detectable, e.g., by visual or instrumental means. In this aspect, a label can be any signal-generating moiety. As used herein, the label (or signal-generating moiety) produces a measurable signal which is detectable by external means, e.g., by the measurement of electromagnetic radiation, and, depending on the system employed, the level of signal can vary to the extent the label is in the environment of the solid support, e.g., an electrode, microparticle or bead. Various labels include signal-producing substances, such as enzymes (horseradish peroxidase, alkaline phosphatase, alkaline peroxidase, glucose 6-phosphate dehydrogenase, and the like), chromophores or chromogens (e.g., dyes that absorb light in the ultraviolet or visible region, phosphors, fluorescers, fluorophores (e.g., fluorescent proteins (green fluorescent protein, yellow fluorescent protein, red fluorescent protein, cyan fluorescent protein); phycobilins (phycoerythrin, R-Phycoerythrin, B-Phycoerythrin); Xanthene derivatives (fluorescein, rhodamine, Oregon green, eosin, Texas red); cyanine derivatives (cyanine, Cy dyes, indocarbocyanine, oxacarbocyanine, thiacarbocyanine, merocyanine); naphthalene derivatives (dansyl and prodan derivatives); coumarin derivatives; oxadiazole derivatives (pyridyloxazole, nitrobenzoxadiazole, benzoxadiazole); Pyrene derivatives (cascade blue); oxazine derivatives (Nile red, Nile blue, cresyl violet, oxazine 170); acridine derivatives (proflavin, acridine orange, acridine yellow); arylmethine derivatives (auramine, crystal violet, malachite green); tetrapyrrole derivatives (porphin, phtalocyanine, bilirubin)), luminophores, chemiluminescent compounds, radioactive compounds, and the like). Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. For example, enzymes can be employed to produce a signal or to amplify a signal or both of the foregoing. As another example, the moiety may be a so-called quencher or an entity upon which a quencher acts. Use of the term "detectably-labeled" is intended to encompass these, and other means, of such labeling.

"Patient" and "subject" may be used interchangeably herein to refer to an animal, such as a bird (e.g., a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, and a mouse) and a primate (for example, a monkey, a chimpanzee, and a human). Preferably, the patient or subject is a human, such as a human suspected of having, diagnosed as having, or undergoing prophylactic or therapeutic treatment for an analyte deficiency or the presence or excess of analyte.

"Patient sample," "test sample," and "sample" may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. In the context of the present disclosure, the sample is preferably serum or plasma and most preferably serum.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte-binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Quality control reagents" in the context of assays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

"Specific binding partner" is a member of a specific binding pair. A specific binding pair comprises two different molecules, which specifically bind to each other through chemical or physical means. Therefore, in addition to analyte/analyte-binding molecules, and antigen/antibody specific binding pairs of common assays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Specific" and "specificity" in the context of an interaction between members of a specific binding pair (e.g., an antigen (or a fragment thereof) and an antibody (or antigenically reactive fragment thereof)) refer to the selective reactivity of the interaction.

The phrase "specifically binds to" and analogous phrases refer to the ability of a first member of a specific binding pair (e.g., an antibody or antigenically reactive fragment thereof) to bind to a second member of a specific binding pair (e.g., an antigen) and not bind specifically to other antigens (or fragments thereof). In the context of the present disclosure an antibody that specifically binds to analyte is considered specific for analyte "Tracer" refers to an analyte or analyte fragment attached to a label, wherein the analyte attached to the label can effectively compete with the analyte for sites on an analyte-binding molecule specific for the analyte.

The above terminology is provided for the purpose of describing particular embodiments. The terminology is not intended to be limiting.

1. Introduction

The internal calibrator kits and assay methods provided herein are particularly suitable to sandwich assay formats. The calibrator set is replaced with a single tracer (i.e., a tracer analyte attached to a label or reporter molecule). A predetermined concentration of the same tracer is also added to each tested sample serving as the internal calibrator. Employing a tracer analyte allows for the use of only a single internal calibrator that can be applied to the determination and analysis of one or more data sets. For instance, the internal calibrator can be run or determined once in a day and used for analyzing subsequent readings, can be run once per week and used for analyzing subsequent readings, or can be run once per month and used for analyzing subsequent readings. Whether or not the calibrator needs to be run or determined again within a set period of time depends on the conditions and circumstances of the assay and would be apparent to one of ordinary skill. However, what the present disclosure provides is a replacement of single internal calibrator for a set of calibrators such that there is no need to run a calibration curve. The benefits of this approach thus are at least two-fold: first, the number of assay runs required to produce a calibrated assay are reduced; and second, the internal calibrator can accommodate and correct for variations in assay conditions, which in turn improves assay precision.

Replacing a whole calibrator set with a single tracer analyte simplifies the calibration procedures and reduces reagent use and assay performance time. The single tracer analyte also serves as an internal calibrator. Generally, the single tracer analyte is premixed with the sample, and forms a tripartite "sandwich" complex concurrently binding to capture and detection analyte-binding molecules in competition with the test analyte. The signal intensity of bound tracer analyte reflects any variation in assay conditions (e.g., matrix, temperature, reaction time, microparticle loss, reagent stability etc). The signal intensity ratio of the bound tracer analyte and bound detection analyte-binding molecule automatically corrects for reaction condition variations.

The assays and methods described herein eliminate the need for using multiple external calibrators or for producing a calibration curve. The internal calibrator accounts for variations in assay conditions, therefor reducing the requirement for instrument precision and reagents stability. Use of the internal calibrator further reduces or eliminates the concerns with calibration curve stability.

Generally, for using the labeled tracer analyte as an internal calibrator, the signal intensity of a predetermined concentration of tracer analyte in the presence of a saturating concentration of detection analyte-binding molecule is measured, and then the measured value of signal intensity of labeled tracer analyte is evaluated against the intensity value obtained in the presence of a test sample suspected of containing test analyte. In this way, a single point calibration value is provided that can be used for the determination of analyte concentrations of numerous sequentially assessed test samples.

In a particular embodiment for the generation of a single point calibration value, the method comprises:

a) contacting a capture analyte-binding molecule with a predetermined concentration of tracer analyte labeled with a first label and a predetermined concentration of detection analyte-binding molecule labeled with a second label, wherein the capture analyte-binding molecule and the detection analyte-binding molecule concurrently bind to the tracer analyte;

b) measuring the signal intensities obtained of the first label ($I_1^0$) and of the second label ($I_2^0$); and c) determining a correction factor (F) as the ratio of the intensity of the second label ($I_2^0$) to the intensity of the first label ($I_1^0$);

$$F = \frac{I_2^0}{I_1^0}.$$

Also provided herein is a method of determining the concentration of analyte in one or more test samples. In one embodiment, the method comprises:

a) contacting a capture analyte-binding molecule with a predetermined concentration of tracer analyte labeled with a first label and a predetermined concentration of detection analyte-binding molecule labeled with a second label in either the absence or presence of one or more test samples that may comprise test analyte, wherein the capture analyte-binding molecule and the detection analyte-binding molecule concurrently bind to the tracer analyte and, if present, to test analyte in said one or more test samples;

b) measuring the signal intensities obtained in the absence of said one or more test samples of the first label ($I_1^0$) and the second label ($I_2^0$);

c) determining a correction factor (F) as the ratio of the intensity of the second label ($I_2^0$) to the intensity of the first label ($I_1^0$);

d) measuring the signal intensities obtained in the presence of said one or more test samples of the first label ($I_1$) and the second label ($I_2$); and e) determining the concentration of test analyte in said one or more test samples by dividing the ratio of the intensity of the second label ($I_2$) to the intensity of the first label ($I_1$) by the correction factor (F) and subtracting the predetermined concentration of tracer analyte;

$$[\text{analyte}] = \frac{I_2 \times [\text{tracer}]}{I_1 \times F} - [\text{tracer}].$$

Employing the foregoing method, numerous test samples (e.g., from about 2 to about 200,000, from about 2 to about 20,000, from about 2 to about 2,000, from about 2 to about 200, or from about 2 to about 20) can be evaluated using a single calibration value and without the need for generation of a calibration curve.

2. Tracer Analytes

In varying embodiments, the tracer analyte employed as internal calibrator is the analyte of interest, or a fragment or mimetic thereof, that can form a complex with a capture analyte-binding molecule and a detection analyte-binding molecule in a sandwich assay. As appropriate, protein analytes can be purified from natural sources or produced by recombinant or synthetic means, as described herein and known in the art. Non-protein analytes can be produced by chemical and synthetic (including biosynthetic) means known to those of skill in the art. The tracer analyte can be attached directly or indirectly to a label.

The label can be any detectable label, as described herein. Illustrative labels include, e.g., fluorophore, radioactive moiety, enzyme, biotin/avidin label, chromophore, chemiluminescent label, or the like. Any suitable detectable label as is known in the art can be used. For example, the detectable label can be a radioactive label (such as $^3H$, $^{125}I$, $^{35}S$, $^{14}C$, $^{32}P$, and $^{33}P$), an enzymatic label (e.g., horseradish peroxidase, alkaline phosphatase, alkaline peroxidase, glucose 6-phosphate dehydrogenase, and the like), a chemiluminescent label (e.g., acridinium esters, thioesters, or sulfonamides; luminol, isoluminol, phenanthridinium esters, and the like), one or more chromophores, e.g., one or more dyes which emit light in the ultraviolet or visible region, phosphors, fluorescers, fluorophores (e.g., fluorescent proteins (green fluorescent protein, yellow fluorescent protein, red fluorescent protein, cyan fluorescent protein); phycobilins (phycoerythrin, R-Phycoerythrin, B-Phycoerythrin); Xanthene derivatives (fluorescein, rhodamine, Oregon green, eosin, Texas red); cyanine derivatives (cyanine, Cy dyes, indocarbocyanine, oxacarbocyanine, thiacarbocyanine, merocyanine); naphthalene derivatives (dansyl and prodan derivatives); coumarin derivatives; oxadiazole derivatives (pyridyloxazole, nitrobenzoxadiazole, benzoxadiazole); Pyrene derivatives (cascade blue); oxazine derivatives (Nile red, Nile blue, cresyl violet, oxazine 170); acridine derivatives (proflavin, acridine orange, acridine yellow); arylmethine derivatives (auramine, crystal violet, malachite green); tetrapyrrole derivatives (porphin, phtalocyanine, bilirubin)), luminophores, chemiluminescers, a fluorescent label (e.g., fluorescein (e.g., 5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, and the like)), rhodamine, quantum dots (e.g., zinc sulfide-capped cadmium selenide), a thermometric label, or an immuno-polymerase chain reaction label. In varying embodiments, the tracer analyte is labeled with a phycobilin (e.g., phycoerythrin, R-Phycoerythrin, B-Phycoerythrin). In some embodiments, the tracer analyte is labeled with an acridinium compound, e.g., acridinium-9-carboxamide, at least one acridinium-9-carboxylate aryl ester, or any combination thereof.

3. Analytes

The kits and methods provided herein are useful for detecting any analyte of interest. Illustrative analytes of interest include without limitation, e.g., proteins, peptides, polypeptides, oligonucleotides or polynucleotides generally, as well as more specifically, e.g., antibodies, antigens, haptens, hormones, drugs, enzymes, or receptors. As appropriate, commercially available analyte-binding molecules (e.g., antibodies or antigenically reactive fragments thereof) can be used in the presently described kits and assays, or analyte-binding molecules (e.g., antibodies or antigenically reactive fragments thereof) can be generated using methods known in the art. Generally, analytes detected using the herein described kits and methods can be detected by sandwich assay.

Illustrative analytes of interest to be detected using the present kits and assay methods include without limitation, e.g., cytokines, immunosuppressant drugs, cardiovascular disease antigens, cancer antigens, infectious disease antigens, pharmacologic agents, hormones, plasma, serum and/or blood antigens, biomarkers (e.g., for kidney injury), vitamins and autoimmune antigens. Such analytes include but are not limited to e.g.: cytokines, immunosuppressant drugs (e.g., sirolimus, tacrolimus, everolimus, temsorolimus, zotarolimus, cyclosporine, or analogs of any of these compounds); cardiovascular disease antigens (e.g., troponin I, cardiac troponin I (cTnI), serum creatine kinase MB isozyme (CKMB), Basic or B-type natriuretic peptide (BNP), galectin-3, myeloperoxidase (MPO), myoglobin, D-dimer fibrin degradation product (or FDP), high sensitivity C-reactive protein); cancer antigens (e.g., prostate-specific antigen (PSA), alfa-fetoprotein (AFP), CA 125, CA 15-3, CA 19-9, Carcinoembryonic antigen (CEA), cytokeratin 19, cytokeratin fragment 21-1 (CYFRA. 21-1), Human epididymis protein 4 (HE4), Progastrin-releasing peptide (ProGRP), Squamous cell carcinoma antigen (SCC-Ag)); infectious disease antigens (e.g., cytomegalovirus (CMV) IgG, CMV IgM, Rubella IgG, Rubella IgM, Toxoplasma IgG, Toxoplasma IgM, Hepatitis A virus (HAV) IgG, HAV IgM, Hepatitis B core protein (HBc), HBc IgM, hepatitis B surface antigen (HBsAg), hepatitis B e antigen (HBeAg), Hepatitis C Virus (HCV, human immunodeficiency virus (HIV)), Chagas, Epstein Barr Virus (EBV), syphilis, Human T-lymphotropic virus (HTLV), Antistreptolysin O (ASO)); pharmacologic agents (e.g., Acetaminophen, Amphetamine/Methamphetamine, Barbiturates, Benzodiazepines, Cannabinoids, Cocaine, Ecstasy, Ethanol, Methadone, Opiates, Phencyclidine (PCP), Propoxyphene, Salicylate, Tricyclic Antidepressants, Amikacin, Carbamazepine, Digitoxin, Digoxin, Gentamicin, Lithium, Phenobarbital, Phenytoin, Quinidine, Theophylline, Tobramycin, Valproic Acid, Vancomycin); hormones (e.g., Dehydroepiandrosterone sulfate (DHEA-S), Estradiol, follicle stimulating hormone (FSH), human chorionic gonadotropin (hCG), luteinizing hormone (LH), Progesterone, Prolactin, Sex hormone-binding globulin (SHBG), Testosterone, cortisol, insulin, pepsinogen I, pepsinogen II, C-peptide, Parathyroid hormone (PTH), thyroid hormone T3, thyroid hormone T4, thyroid stimulating hormone), enzymes (e.g., Acid Phosphatase, Alanine Aminotransferase, Alkaline Phosphatase, Amylase, Aspartate Aminotransferase, Creatine Kinase, Gamma-Glutamyl Transferase (GGT), Lactate Dehydrogenase (LDH), α hydroxybutyrate dehydrogenase (α HBDH), Lipase; Cholinesterase, Ceruloplasmin); plasma, serum and/or blood antigens (e.g., Albumin, microalbumin, prealbumin, Creatinine, Cystatin C, Bilirubin, Lipoprotein(a) [Lp(a)], low density lipoprotein (LDL), high density lipoprotein (HDL), Apolipoprotein A1, Apolipoprotein B, Complement C3, Complement C4, Haptoglobin, Immunoglobulin A (IgA), Immunoglobulin E (IgE), Immunoglobulin G (IgG), Immunoglobulin M (IgM), Kappa Light Chain, Lambda Light Chain, Beta2 Microglobulin, hemoglobin, homocysteine, C-reactive protein (CRP)); biomarkers (e.g., for kidney injury, e.g., neutrophil gelatinase-associated lipocalin (NGAL)); vitamins (e.g., vitamin B12, folate, vitamin D); Anti-cyclic citrullinated peptide (anti-CCP) antibody, Alpha-1 antitrypsin (AAT), Alpha-1 Glycoprotein, autoimmune antigens (e.g., Rheumatoid Factor (RF), Anti-Thyroglobulin (Anti-Tg), and Anti-thyroid peroxidase antibodies (anti-TPO antibodies)).

4. Analyte-Binding Molecules

Generally, the kits and assays described herein employ two analyte-binding molecules, wherein the analyte-binding molecules complex with the analyte and/or the tracer analyte. The two analyte-binding molecules that complex with the analyte and/or the tracer analyte can bind the analyte with either the same or different affinities, e.g., from about 3-fold to about 5-fold, from about 5-fold to about 100-fold, from about 5-fold to about 10-fold, from about 10-fold to about 25-fold, from about 25-fold to about 50-fold, from about 50-fold to about 100-fold, with about 3-fold, about 5-fold, about 10-fold, about 25-fold, about 50-fold, about 100-fold, or more-fold differences in affinities for binding to the analyte. In varying embodiments, one or both of the analyte-binding molecules are bound directly or indirectly to a label. In varying embodiments, one or both of the analyte-binding molecules are antibodies or antigenically reactive fragments (i.e., that bind analyte) thereof.

In some embodiments, one or both of the capture and detection analyte-binding molecules are non-antibody analyte-binding molecules. Other compounds have been developed that target and bind to targets in a manner similar to antibodies. Certain of these "antibody mimics" use non-immunoglobulin protein scaffolds as alternative protein frameworks for the variable regions of antibodies.

For example, Ladner et al. (U.S. Pat. No. 5,260,203) describe single polypeptide chain binding molecules with binding specificity similar to that of the aggregated, but molecularly separate, light and heavy chain variable region of antibodies. The single-chain binding molecule contains the antigen binding sites of both the heavy and light variable regions of an antibody connected by a peptide linker and will fold into a structure similar to that of the two peptide antibody. The single-chain binding molecule displays several advantages over conventional antibodies, including, smaller size, greater stability and are more easily modified.

Ku et al. (*Proc. Natl. Acad. Sci. U.S.A.* 92(14):6552-6556 (1995)) discloses an alternative to antibodies based on cytochrome b562. Ku et al. (1995) generated a library in which two of the loops of cytochrome b562 were randomized and selected for binding against bovine serum albumin. The individual mutants were found to bind selectively with BSA similarly with anti-BSA antibodies.

Lipovsek et al. (U.S. Pat. Nos. 6,818,418 and 7,115,396) discloses an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted analyte. Any technique for evolving new or improved binding proteins can be used with these antibody mimics.

The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are therefore, stable under conditions which would normally break down antibodies. In addition, since the structure of these fibronectin-based antibody mimics is similar to that of the IgG heavy chain, the process for loop randomization and shuffling can be employed in vitro that is similar to the process of affinity maturation of antibodies in vivo.

Beste et al. (*Proc. Natl. Acad. Sci. U.S.A.* 96(5): 1898-1903 (1999)) discloses an antibody mimic based on a lipocalin scaffold (Anticalin®). Lipocalins are composed of a β-barrel with four hypervariable loops at the terminus of the protein. Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Anticalins® are small, single chain peptides, typically between 160 and 180 residues, which provide several advantages over antibodies, including decreased cost of production, increased stability in storage and decreased immunological reaction.

Hamilton et al. (U.S. Pat. No. 5,770,380) discloses a synthetic antibody mimic using the rigid, non-peptide organic scaffold of calixarene, attached with multiple variable peptide loops used as binding sites. The peptide loops all project from the same side geometrically from the calixarene with respect to each other. Because of this geometric confirmation, all of the loops are available for binding, increasing the binding affinity to an analyte. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (Cell. Mol. Biol. 49(2):209-216 (2003)) discusses a methodology for reducing antibodies into smaller peptidomimetics, they term "antibody like binding peptidomemetics" (ABiP) which can also be useful as an alternative to antibodies.

Silverman et al. (Nat. Biotechnol., 23: 1556-1561 (2005)) discloses fusion proteins that are single-chain polypeptides comprising multiple domains termed "avimers." Developed from human extracellular receptor domains by in vitro exon shuffling and phage display the avimers are a class of binding proteins somewhat similar to antibodies in their affinities and specificities for various target molecules. The resulting multidomain proteins can comprise multiple independent binding domains that can exhibit improved affinity (in some cases sub-nanomolar) and specificity compared with single-epitope binding proteins. Additional details concerning methods of construction and use of avimers are disclosed, for example, in U.S. Patent App. Pub. Nos. 2004-0175756, 2005-0048512, 2005-0053973, 2005-0089932 and 2005-0221384.

Oftentimes, commercially available antibodies or analyte-binding molecules can be used in the present assays. In varying embodiments, one or both of the capture and detection analyte-binding molecules are generated, e.g., using known recombinant and/or monoclonal antibody production techniques.

Monoclonal antibodies can be produced and modified (e.g., conservatively substituted) in accordance with methods known in the art. The ability of a modified antibody, or antigenically reactive fragment thereof, to detect analyte can be determined using any standard method known in the art for assessing antigen binding specificity, including, for example, the methods described and exemplified herein. Such methods include, but are not limited to, ELISA, Western blot, surface plasmon resonance (e.g., BIAcore®), KinExA® (Kinetic Exclusion Assay) assay, and radioimmunoassay. Preferably, the modified antibody, or antigenically reactive fragment, demonstrates analyte binding characteristics that are at least as good as, and preferably (even desirably) better than, the corresponding unmodified antibody.

a. Synthetic Production

Once sequenced, polypeptides, such as a monoclonal antibody (or a fragment thereof), which specifically binds analyte, can be synthesized using methods known in the art, such as, for example, exclusive solid phase synthesis, partial solid phase synthesis, fragment condensation, and classical solution synthesis. See, e.g., Merrifield, J. Am. Chem. Soc. 85: 2149 (1963). On solid phase, the synthesis typically begins from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories (Richmond, Calif.), and the preparation of the hydroxymethyl resin is described by Bodonszky et al., Chem. Ind. (London) 38: 1597 (1966). The benzhydrylamine (BHA) resin has been described by Pietta and Marshall, Chem. Comm. 650 (1970) and is commercially available from Beckman Instruments, Inc. (Palo Alto, Calif.) in the hydrochloride form. Automated peptide synthesizers are commercially available, as are services that make peptides to order.

Thus, the polypeptides can be prepared by coupling an alpha-amino protected amino acid to the chloromethylated resin with the aid of, for example, cesium bicarbonate catalyst, according to the method described by Gisin, Helv. Chim. Acta. 56: 1467 (1973). After the initial coupling, the alpha-amino protecting group is removed by a choice of reagents including trifluoroacetic acid (TFA) or hydrochloric acid (HCl) solutions in organic solvents at room temperature.

Suitable alpha-amino protecting groups include those known to be useful in the art of stepwise synthesis of peptides. Examples of alpha-amino protecting groups are: acyl type protecting groups (e.g., formyl, trifluoroacetyl, and acetyl), aromatic urethane type protecting groups (e.g., benzyloxycarbonyl (Cbz) and substituted Cbz), aliphatic urethane protecting groups (e.g., t-butyloxycarbonyl (Boc), isopropyloxycarbonyl, and cyclohexyloxycarbonyl), and alkyl type protecting groups (e.g., benzyl and triphenylmethyl). Boc and Fmoc are useful protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride and dimethyl formamide (DMF) mixtures.

After the desired amino acid sequence has been completed, the desired peptide is decoupled from the resin support by treatment with a reagent, such as TFA or hydrogen fluoride (HF), which not only cleaves the peptide from the resin, but also cleaves all remaining side chain protecting groups. When the chloromethylated resin is used, HF treatment results in the formation of the free peptide acids. When the benzhydrylamine resin is used, HF treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These and other solid phase peptide synthesis procedures are well-known in the art. Such procedures are also described by Stewart and Young in Solid Phase Peptide Syntheses (2nd Ed., Pierce Chemical Company, 1984).

b. Recombinant Production

A polypeptide, such as a monoclonal antibody (or a fragment thereof) which specifically binds analyte (or fragments thereof), can be recombinantly produced using methods known in the art. For example, an isolated nucleic acid comprising a nucleotide sequence encoding the antibody (or a fragment thereof) can be expressed in a host cell, and the antibody can be isolated. The isolated nucleic acid comprises a nucleotide sequence encoding the amino acid sequence of the antibody against analyte. The isolated nucleic acid can be synthesized with an oligonucleotide synthesizer, for example. One of ordinary skill in the art will readily appreciate that, due to the degeneracy of the genetic code, more than one nucleotide sequence can encode a given amino acid sequence. In this regard, a nucleotide sequence encoding an amino acid sequence that is substantially identical to that of the antibody against analyte can be used, provided that the variant antibody as expressed competes with the antibody against the analyte. Codons, which are favored by a given host cell, preferably are selected for recombinant production. A nucleotide sequence encoding the amino acid sequence of the antibody against the analyte can be combined with other nucleotide sequences using polymerase chain reaction (PCR), ligation, or ligation chain reaction (LCR) to encode an anti-analyte antibody or antigenically reactive fragment thereof. The individual oligonucleotides typically contain 5' or 3' overhangs for complementary assembly. Once assembled, the nucleotide sequence encoding an anti-analyte antibody or antigenically reactive fragment thereof can be inserted into a vector, operably linked to control sequences as necessary for expression in a given host cell, and introduced (such as by transformation or transfection) into a host cell. The nucleotide sequence can be further manipulated (for example, linked to one or more nucleotide sequences encoding additional immunoglobulin domains, such as additional constant regions) and/or expressed in a host cell.

Although not all vectors and expression control sequences may function equally well to express a polynucleotide sequence of interest and not all hosts function equally well with the same expression system, it is believed that those skilled in the art will be able to make a selection among these vectors, expression control sequences, optimized codons, and hosts for use in the present disclosure without any undue experimentation. For example, in selecting a vector, the host must be considered because the vector must be able to replicate in it or be able to integrate into the chromosome. The vector's copy number, the ability to control that copy number, and the expression of any other proteins encoded by the vector, such as antibiotic markers, should also be considered. In selecting an expression control sequence, a variety of factors also can be considered. These include, but are not limited to, the relative strength of the sequence, its controllability, and its compatibility with the nucleotide sequence encoding the anti-analyte antibody, particularly with regard to potential secondary structures. Hosts should be selected by consideration of their compatibility with the chosen vector, their codon usage, their secretion characteristics, their ability to fold the polypeptide correctly, their fermentation or culture requirements, their ability (or lack thereof) to glycosylate the protein, and the ease of purification of the products encoded by the nucleotide sequence, etc.

The recombinant vector can be an autonomously replicating vector, namely, a vector existing as an extrachromosomal entity, the replication of which is independent of chromosomal replication (such as a plasmid). Alternatively, the vector can be one which, when introduced into a host cell, is integrated into the host cell genome and replicated together with the chromosome(s) into which it has been integrated.

The vector is preferably an expression vector in which the polynucleotide sequence encoding the anti-analyte antibody is operably linked to additional segments required for transcription of the polynucleotide sequence. The vector is typically derived from plasmid or viral DNA. A number of suitable expression vectors for expression in the host cells mentioned herein are commercially available or described in the literature. Useful expression vectors for eukaryotic hosts, include, but are not limited to, vectors comprising expression control sequences from SV40, bovine papilloma virus, adenovirus and cytomegalovirus. Specific vectors include pCDNA3.1 (+)\Hyg (Invitrogen Corp., Carlsbad, Calif.) and pCI-neo (Stratagene, La Jolla, Calif.). Examples of expression vectors for use in yeast cells include, but are not limited to, the 2μ plasmid and derivatives thereof, the POT1 vector (see, e.g., U.S. Pat. No. 4,931,373), the pJSO37 vector (described in Okkels, Ann. New York Acad. Sci. 782: 202-207 (1996)) and pPICZ A, B or C (Invitrogen). Examples of expression vectors for use in insect cells include, but are not limited to, pVL941, pBG311 (Cate et al., Cell 45: 685-698 (1986)), and pBluebac 4.5 and pMelbac (both of which are available from Invitrogen).

Other vectors that can be used allow the nucleotide sequence encoding the anti-analyte antibody to be amplified in copy number. Such amplifiable vectors are well-known in the art. These vectors include, but are not limited to, those vectors that can be amplified by dihydrofolate reductase (DHFR) amplification (see, for example, Kaufman, U.S. Pat. No. 4,470,461; and Kaufman et al., Mol. Cell. Biol. 2: 1304-1319 (1982)) and glutamine synthetase (GS) amplification (see, for example, U.S. Pat. No. 5,122,464 and European Pat. App. Pub. No. 0 338 841).

The recombinant vector can further comprise a nucleotide sequence enabling the vector to replicate in the host cell in question. An example of such a sequence for use in a mammalian host cell is the SV40 origin of replication. Suitable sequences enabling the vector to replicate in a yeast cell are the yeast plasmid 2μ replication genes REP 1-3 and origin of replication.

The vector can also comprise a selectable marker, namely, a gene or polynucleotide, the product of which complements a defect in the host cell, such as the gene coding for DHFR or the *Schizosaccharomyces pombe* TPI gene (see, e.g., Russell, Gene 40: 125-130 (1985)), or one which confers resistance to a drug, such as ampicillin, kanamycin, tetracycline, chloramphenicol, neomycin, hygromycin or methotrexate. For filamentous fungi, selectable markers include, but are not limited to, amdS, pyrG, arcB, niaD and sC.

Also present in the vector are "control sequences," which are any components that are necessary or advantageous for the expression of the anti-analyte antibody. Each control sequence can be native or foreign to the nucleotide sequence encoding the anti-analyte antibody. Such control sequences include, but are not limited to, a leader, a polyadenylation sequence, a propeptide sequence, a promoter, an enhancer or an upstream activating sequence, a signal peptide sequence, and a transcription terminator. At a minimum, the control sequences include at least one promoter operably linked to the polynucleotide sequence encoding the anti-analyte antibody.

By "operably linked" is meant the covalent joining of two or more nucleotide sequences, by means of enzymatic ligation or otherwise, in a configuration relative to one another such that the normal function of the sequences can be performed. For example, a nucleotide sequence encoding a presequence or secretory leader is operably linked to a nucleotide sequence for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in the same reading frame. Linking is accomplished by ligation at convenient restriction sites. If such sites do not exist, then synthetic oligonucleotide adaptors or linkers can be used, in conjunction with standard recombinant DNA methods.

A wide variety of expression control sequences can be used in the context of the present disclosure. Such useful expression control sequences include the expression control sequences associated with structural genes of the foregoing expression vectors as well as any sequence known to control the expression of genes of prokaryotic or eukaryotic cells or their viruses, and various combinations thereof. Examples of suitable control sequences for directing transcription in mammalian cells include the early and late promoters of SV40 and adenovirus, for example, the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, J. Mol. Biol. 196: 947-50 (1987)).

In order to improve expression in mammalian cells a synthetic intron can be inserted in the 5' untranslated region of a polynucleotide sequence encoding the antibody or a fragment thereof. An example of a synthetic intron is the synthetic intron from the plasmid pCI-Neo (available from Promega Corporation, Madison, Wis.).

Examples of suitable control sequences for directing transcription in insect cells include, but are not limited to, the polyhedrin promoter, the P10 promoter, the baculovirus immediate early gene 1 promoter, the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulas* glucoamylase, *A. nidulans* acetamidase, *Rhizomucor miehei* aspartic proteinase or lipase, the TPI1 terminator, and the ADH3 terminator.

The polynucleotide sequence encoding the antibody of interest may or may not also include a polynucleotide sequence that encodes a signal peptide. The signal peptide is present when the anti-analyte antibody is to be secreted from the cells in which it is expressed. Such signal peptide, if present, should be one recognized by the cell chosen for expression of the polypeptide. The signal peptide can be homologous or heterologous to the anti-analyte monoclonal antibody or can be homologous or heterologous to the host cell, i.e., a signal peptide normally expressed from the host cell or one which is not normally expressed from the host cell. Accordingly, the signal peptide can be prokaryotic, for example, derived from a bacterium, or eukaryotic, for example, derived from a mammalian, insect, filamentous fungal, or yeast cell.

The presence or absence of a signal peptide will, for example, depend on the expression host cell used for the production of the anti-analyte antibody. For use in filamentous fungi, the signal peptide can conveniently be derived from a gene encoding an *Aspergillus* sp. amylase or glucoamylase, a gene encoding a *Rhizomucor miehei* lipase or protease or a *Humicola lanuginosa* lipase. For use in insect cells, the signal peptide can be derived from an insect gene (see, e.g., Int'l Pat. App. Pub. No. WO 90/05783), such as the lepidopteran Manduca sexta adipokinetic hormone precursor (see, e.g., U.S. Pat. No. 5,023,328), the honeybee melittin (Invitrogen), ecdysteroid UDP glucosyltransferase (egt) (Murphy et al., Protein Expression and Purification 4: 349-357 (1993)), or human pancreatic lipase (hpl) (Methods in Enzymology 284: 262-272 (1997)).

Specific examples of signal peptides for use in mammalian cells include murine Ig kappa light chain signal peptide (Coloma, J. Imm. Methods 152: 89-104 (1992)). Suitable signal peptides for use in yeast cells include the α-factor signal peptide from *S. cerevisiae* (see, e.g., U.S. Pat. No. 4,870,008), the signal peptide of mouse salivary amylase (see, e.g., Hagenbuchle et al., Nature 289: 643-646 (1981)), a modified carboxypeptidase signal peptide (see, e.g., Valls et al., Cell 48: 887-897 (1987)), the yeast BAR1 signal peptide (see, e.g., Int'l Pat. App. Pub. No. WO 87/02670), and the yeast aspartic protease 3 (YAP3) signal peptide (see, e.g., Egel-Mitani et al., Yeast 6: 127-137 (1990)).

Any suitable host can be used to produce the anti-analyte antibody, including bacteria, fungi (including yeasts), plant, insect, mammal or other appropriate animal cells or cell lines, as well as transgenic animals or plants. Examples of bacterial host cells include, but are not limited to, gram-positive bacteria, such as strains of *Bacillus*, for example, *B. brevis* or *B. subtilis, Pseudomonas* or *Streptomyces*, or gram-negative bacteria, such as strains of *E. coli*. The introduction of a vector into a bacterial host cell can, for instance, be effected by protoplast transformation (see, for example, Chang et al., Molec. Gen. Genet. 168: 111-115 (1979)), using competent cells (see, for example, Young et al., J. of Bacteriology 81: 823-829 (1961), or Dubnau et al., J. of Molec. Biol. 56: 209-221 (1971)), electroporation (see, for example, Shigekawa et al., Biotechniques 6: 742-751 (1988)), or conjugation (see, for example, Koehler et al., J. of Bacteriology 169: 5771-5278 (1987)).

Examples of suitable filamentous fungal host cells include, but are not limited to, strains of *Aspergillus*, for example, *A. oryzae, A. niger*, or *A. nidulans, Fusarium* or *Trichoderma*. Fungal cells can be transformed by a process involving protoplast formation, transformation of the protoplasts, and regeneration of the cell wall using techniques known to those ordinarily skilled in the art. Suitable procedures for transformation of *Aspergillus* host cells are described in European Pat. App. Pub. No. 238 023 and U.S. Pat. No. 5,679,543. Suitable methods for transforming *Fusarium* species are described by Malardier et al., Gene 78: 147-156 (1989), and Int'l Pat. App. Pub. No. WO 96/00787. Yeast can be transformed using the procedures described by Becker and Guarente, In Abelson, J. N. and Simon, M. I., editors, Guide to Yeast Genetics and Molecular Biology, Methods in Enzymology 194: 182-187, Academic Press, Inc., New York; Ito et al, J. of Bacteriology 153: 163 (1983); and Hinnen et al., PNAS USA 75: 1920 (1978).

Examples of suitable yeast host cells include strains of *Saccharomyces*, for example, *S. cerevisiae, Schizosaccharomyces, Klyveromyces, Pichia*, such as *P. pastoris* or *P. methanolica, Hansenula*, such as *H. polymorpha* or *yarrowia*. Methods for transforming yeast cells with heterologous polynucleotides and producing heterologous polypeptides therefrom are disclosed by Clontech Laboratories, Inc, Palo Alto, Calif., USA (in the product protocol for the Yeastmaker™ Yeast Tranformation System Kit), and by Reeves et al., FEMS Microbiology Letters 99: 193-198 (1992), Manivasakam et al., Nucleic Acids Research 21: 4414-4415 (1993), and Ganeva et al., FEMS Microbiology Letters 121: 159-164 (1994).

Examples of suitable insect host cells include, but are not limited to, a Lepidoptora cell line, such as *Spodoptera frugiperda* (Sf9 or Sf21) or *Trichoplusia ni* cells (High Five) (see, e.g., U.S. Pat. No. 5,077,214). Transformation of insect cells and production of heterologous polypeptides are well-known to those skilled in the art.

Examples of suitable mammalian host cells include Chinese hamster ovary (CHO) cell lines, simian (e.g., Green Monkey) cell lines (COS), mouse cells (for example, NS/O), baby hamster kidney (BHK) cell lines, human cells (such as human embryonic kidney (HEK) cells (e.g., HEK 293 cells (A.T.C.C. Accession No. CRL-1573))), myeloma cells that do not otherwise produce immunoglobulin protein, and plant cells in tissue culture. Preferably, the mammalian host cells are CHO cell lines and HEK 293 cell lines. Another host cell is the B3.2 cell line (e.g., Abbott Laboratories, Abbott Bioresearch Center), or another dihydrofolate reductase deficient (DHFR-) CHO cell line (e.g., available from Invitrogen).

Methods for introducing exogenous polynucleotides into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamine™ 2000. These methods are well-known in the art and are described, for example, by Ausbel et al. (eds.), Current Protocols in Molecular Biology, John Wiley & Sons, New York, USA (1996). The cultivation of mammalian cells is conducted according to established methods, e.g., as disclosed in Jenkins, Ed., Animal Cell Biotechnology, Methods and Protocols, Human Press Inc. Totowa, N.J., USA (1999), and Harrison and Rae, General Techniques of Cell Culture, Cambridge University Press (1997).

In the production methods, cells are cultivated in a nutrient medium suitable for production of the anti-analyte antibody using methods known in the art. For example, cells are cultivated by shake flask cultivation, small-scale or large-scale fermentation (including continuous, batch, fed-batch, or solid state fermentations) in laboratory or industrial fermenters performed in a suitable medium and under conditions allowing the anti-human analyte monoclonal antibody to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the anti-analyte antibody is secreted into the nutrient medium, it can be recovered directly from the medium. If the anti-analyte antibody is not secreted, it can be recovered from cell lysates.

The resulting anti-analyte antibody can be recovered by methods known in the art. For example, the anti-analyte antibody can be recovered from the nutrient medium by conventional procedures including, but not limited to, centrifugation, filtration, extraction, spray drying, evaporation, or precipitation.

The anti-analyte antibody can be purified by a variety of procedures known in the art including, but not limited to, chromatography (such as, but not limited to, ion exchange, affinity, hydrophobic, chromatofocusing, and size exclusion), electrophoretic procedures (such as, but not limited to, preparative isoelectric focusing), differential solubility (such as, but not limited to, ammonium sulfate precipitation), SDS-PAGE, or extraction (see, for example, Janson and Ryden, editors, Protein Purification, VCH Publishers, New York (1989)).

c. Antibody Production by Immunization, Hybridomas or Other Means

Other antibodies (or fragments thereof) that specifically bind to analyte (or fragments thereof) can be made using a variety of different techniques known in the art. For example, polyclonal and monoclonal antibodies can be raised by immunizing a suitable subject (such as, but not limited to, a rabbit, a goat, a mouse, or other mammal) with an immunogenic preparation, which contains a suitable immunogen. The immunogen can be enriched/purified and isolated from a cell that produces it using affinity chromatography, immune-precipitation or other techniques, which are well-known in the art. Alternatively, immunogen can be prepared using chemical synthesis using routine techniques known in the art (such as, but not limited to, a synthesizer). The antibodies raised in the subject can then be screened to determine if the antibodies bind to the immunogen (or a fragment thereof).

The unit dose of immunogen (namely, the purified protein, tumor cell expressing the protein, or recombinantly expressed immunogen (or a fragment or a variant (or a fragment thereof) thereof) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen.

Other methods of raising antibodies include using transgenic mice, which express human immunoglobin genes (see, for example, Int'l Pat. App. Pub. Nos. WO 91/00906, WO 91/10741, and WO 92/03918). Alternatively, human monoclonal antibodies can be produced by introducing an antigen into immune-deficient mice that have been engrafted with human antibody-producing cells or tissues (for example, human bone marrow cells, peripheral blood lymphocytes (PBL), human fetal lymph node tissue, or hematopoietic stem cells). Such methods include raising antibodies in SCID-hu mice (see, for example, Int'l Pat. App. Pub. No. WO 93/05796; U.S. Pat. No. 5,411,749; or McCune et al., Science 241: 1632-1639 (1988)) or Rag-1/Rag-2 deficient mice. Human antibody-immune deficient mice are also commercially available. For example, Rag-2 deficient mice are available from Taconic Farms (Germantown, N.Y.).

Monoclonal antibodies can be generated by immunizing a subject with an immunogen. At the appropriate time after immunization, for example, when the antibody titers are at a sufficiently high level, antibody-producing cells can be harvested from an immunized animal and used to prepare monoclonal antibodies using standard techniques. For example, the antibody-producing cells can be fused by standard somatic cell fusion procedures with immortalizing cells, such as myeloma cells, to yield hybridoma cells. Such techniques are well-known in the art, and include, for example, the hybridoma technique as originally developed by Kohler and Milstein, Nature 256: 495-497 (1975)), the human B cell hybridoma technique (Kozbar et al., Immunology Today 4: 72 (1983)), and the Epstein-Barr virus (EBV)-hybridoma technique to produce human monoclonal antibodies (Cole et al., Monoclonal Antibodies and Cancer Therapy, Alan R. Liss, Inc. pp. 77-96 (1985)). The technology for producing monoclonal antibody hybridomas is well-known to those skilled in the art.

Monoclonal antibodies also can be made by harvesting antibody-producing cells, for example, splenocytes, from transgenic mice, which express human immunoglobulin genes and which have been immunized with the immunogen. The splenocytes can be immortalized through fusion with human myelomas or through transformation with EBV. These hybridomas can be made using human B cell- or EBV-hybridoma techniques described in the art (See, for example, Boyle et al., European Pat. Pub. No. 0 614 984).

Hybridoma cells producing a monoclonal antibody, which specifically binds to the immunogen, are detected by screening the hybridoma culture supernatants by, for example, screening to select antibodies that specifically bind to the immobilized immunogen (or a fragment thereof), or by testing the antibodies as described herein to determine if the antibodies have the desired characteristics, namely, the ability to bind to immunogen (or a fragment thereof). After hybridoma cells are identified that produce antibodies of the desired specificity, the clones may be subcloned, e.g., by limiting dilution procedures, for example the procedure described by Wands et al. (Gastroenterology 80: 225-232 (1981)), and grown by standard methods.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (See, for example, R. H. Kenneth, in Monoclonal Antibodies: A New Dimension In Biological Analyses, Plenum Publishing Corp., New York, N.Y. (1980)). Conditioned hybridoma culture supernatant containing the antibody can then be collected. The monoclonal antibodies secreted by the subclones optionally can be isolated from the culture medium by conventional immunoglobulin purification procedures such as, for example, protein A chromatography, hydroxylapatite chromatography, gel electrophoresis, dialysis, or affinity chromatography.

Monoclonal antibodies can be engineered by constructing a recombinant combinatorial immunoglobulin library and screening the library with the immunogen or a fragment thereof. Kits for generating and screening phage display libraries are commercially available (See, for example, the Pharmacia Recombinant Phage Antibody System, Catalog No. 27-9400-01; and the Stratagene SurfZAP Phage Display Kit, Catalog No. 240612). Likewise, yeast display vectors are known in the art and are commercially available (for example, pYD1 available from Invitrogen). Briefly, the antibody library is screened to identify and isolate phages or yeast cells that express an antibody that specifically binds to the immunogen or a fragment thereof. Preferably, the primary screening of the library involves screening with an immobilized immunogen or a fragment thereof.

Following screening, the display phage or yeast is isolated and the polynucleotide encoding the selected antibody can be recovered from the display phage or yeast (for example, from the phage or yeast genome) and subcloned into other expression vectors (e.g., into Saccharomyces cerevesiae cells, for example EBY100 cells (Invitrogen)) by well-known recombinant DNA techniques. The polynucleotide can be further manipulated (for example, linked to nucleic acid encoding additional immunoglobulin domains, such as additional constant regions) and/or expressed in a host cell.

Once a monoclonal antibody that specifically binds to analyte is obtained in accordance with methods described above, it can be sequenced in accordance with methods known in the art. The antibody then can be made using recombinant DNA technology, chemical synthesis, or a combination of chemical synthesis and recombinant DNA technology as described above.

Furthermore, in some aspects of the disclosure, it may be possible to employ commercially available anti-analyte antibodies or methods for production of anti-analyte antibodies as described in the literature. Alternatively, anti-analyte antibodies can be produced using methods described in the literature.

d. Antibody Fragments

An antigenically reactive fragment of an antibody that binds to analyte also can be used as described herein. The antibody fragment can be a Fab, a Fab', a Fab'-SH fragment, a di-sulfide linked Fv, a single chain Fv (scFv), a F(ab')2 fragment, and the like. Various techniques are known to those skilled in the art for the production of antibody fragments. For example, such fragments can be derived via proteolytic digestion of intact antibodies (see, for example, Morimoto et al., J. Biochem. Biophys. Methods 24: 107-117 (1992), and Brennan et al., Science 229: 81 (1985)) or produced directly by recombinant host cells. For example, Fab'-SH fragments can be directly recovered from E. coli and chemically coupled to form F(ab')2 fragments (see, e.g., Carter et al., Bio/Technology 10: 163-167 (1992)). In another embodiment, the F(ab')2 is formed using the leucine zipper GCN4 to promote assembly of the F(ab')2 molecule. Alternatively, Fv, Fab or F(ab')2 fragments can be isolated directly from recombinant host cell culture. Single chain variable region fragments (scFv) are made by linking light and/or heavy chain variable regions by using a short linking peptide or sequence (see, e.g., Bird et al., Science 242: 423-426 (1998)). The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art. Moreover, other forms of single-chain antibodies, such as diabodies are also contemplated by the present disclosure. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see, for example, Holliger et al., PNAS USA 90: 6444-6448 (1993); and Poljak et al., Structure 2: 1121-1123 (1994)).

The antibody and antigenically reactive fragment thereof have a variety of uses. In one aspect, the antibody (or a fragment thereof) can be used as one or more immunodiagnostic reagents. For example, the antibodies can be used as one or more immunodiagnostic reagents in one or more methods for detecting the presence of analyte in a test sample. More specifically, the antibody (or antigenically reactive fragment thereof) can be used as a capture antibody or a detection antibody in an assay to detect the presence of analyte in a test sample.

5. Kits

Kits for assaying a test sample for analyte (or a fragment thereof) are also provided. Generally, the kits comprise a tracer analyte (i.e., employed as an internal calibrator as described herein), a capture analyte-binding molecule, and a detection analyte-binding molecule useful together for assaying the test sample for an analyte of interest and instructions for assaying the test sample for analyte. In varying embodiments, the kits can comprise a tracer analyte comprising a first label, a capture analyte-binding molecule, and a detection analyte-binding molecule comprising a second label, wherein the capture analyte-binding molecule and the detection analyte-binding molecule can concurrently bind to the tracer analyte and/or the test analyte.

As those of skill in the art understand, the components described below with respect to kits are also useful in the methods described herein. Thus, the following description of solid supports and labels apply equally to the kits and methods described herein.

In varying embodiments, the kit can comprise instructions for assaying the test sample for analyte (or fragments thereof) by an assay described herein, e.g., a microparticle assay. The instructions can be in paper form or computer-readable form, such as a disk, CD, DVD, or the like. Alternatively or additionally, the kit can comprise a calibrator or control, e.g., purified, and optionally lyophilized, analyte (or a fragment thereof), and/or at least one container (e.g., tube, microtiter plates or strips, which can be already coated with one or more analyte-binding molecules) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve or a reference standard for purposes of quantifying analyte.

As appropriate or desired, the kit can contain a solid support, e.g., attached to the capture analyte-binding molecule. Illustrative solid supports include, for example, an electrode, a microparticle, a magnetic particle, bead, test tube, microtiter plate, cuvette, membrane, scaffolding molecule, film, filter paper, disc or chip. Illustrative solid supports include without limitation, e.g., an electrode, a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, or magnetizable microparticles (e.g., microparticles having ferric oxide or chromium oxide cores and homo- or hetero-polymeric coats and radii of about 1-10 microns)). The substrate can comprise a suitable porous material with a suitable surface affinity to bind a capture agent and sufficient porosity to allow access by a detection agent. A microporous material is generally preferred, although a gelatinous material in a hydrated state can be used. Such porous substrates can be in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an analyte-binding molecule to the substrate. Irreversible binding, generally by adsorption through hydrophobic forces, of the capture agent to the substrate results; alternatively, a chemical coupling agent or other means can be used to bind covalently the capture agent to the substrate, provided that such binding does not interfere with the ability of the capture agent to bind analyte.

One support suitable for use herein is a microparticle. Microparticles that are suitable for use with the methods described herein include, without limitation, magnetic microparticles. The sizes of microparticles typically range from about 0.1 to about 100 µm. Commercially available microparticles are available in a wide variety of materials, including those made of ceramics, glass, polymers, and metals. Magnetic microparticles suitable for use in the methods described herein are commercially available, e.g., from Agilent Technologies, Santa Clara, Calif. Although the generally accepted definition of 0.1 to 100 µm complements the size definition of nanoparticles, there are other ways to define the size. General acceptance considers microparticles smaller than 100 nm to be nanoparticles. Any microparticle larger than 0.5 µm and anything smaller than 0.5 mm is considered to be a microparticle. In general, the size of microparticles suitable for use with the method described herein must be sufficiently large so that two microparticles can be resolved by the image system selected. The properties of the microparticles suitable for use with the method described herein, such as, for example, color, is a matter of choice. One of ordinary skill in the art can select the properties of the microparticles in order to fulfill requirements imposed by appropriate variations of the method.

Reaction vessels that are suitable for use with the kits and methods described herein include micro-well plates. In varying embodiments, the reaction vessel can be of such a character that an image of the capture analyte-binding molecule-analyte-detection analyte-binding molecule complex can be made. In one embodiment, the reaction vessel is transparent to electromagnetic radiation, typically in the ultraviolet and the visible range of the spectrum. Materials that are suitable for making a reaction vessel include glass, and polymeric materials. In one embodiment, the material of the reaction vessel is not auto-fluorescent. However, generally, the particular form or shape of the reaction vessel is not critical.

In some embodiments, the capture and/or the detection analyte-binding molecules are bound with microparticles, which have been previously coated with streptavidin or biotin (e.g., using Power-Bind™-SA-MP streptavidin-coated microparticles (Seradyn, Indianapolis, Ind.)) or anti-species-specific monoclonal antibodies. If necessary, the substrate can be derivatized to allow reactivity with various functional groups on the capture agent. Such derivatization requires the use of certain coupling agents, examples of which include, but are not limited to, maleic anhydride, N-hydroxysuccinimide, and 1-ethyl-3-(3-dimethylaminopropyl) carbodiimide. If desired, one or more capture agents (e.g. analyte-binding molecules (e.g., antibodies or antigenically active fragments thereof)), each of which is specific for analyte can be attached to solid supports in different physical or addressable locations (e.g., such as in a biochip configuration (see, e.g., U.S. Pat. No. 6,225,047, Int'l Pat. App. Pub. No. WO 99/51773; U.S. Pat. No. 6,329,209; Int'l Pat. App. Pub. No. WO 00/56934, and U.S. Pat. No. 5,242,828).

The tracer analyte is attached, directly or indirectly, to a first label, and the detection analyte-binding molecule is attached, directly or indirectly, to a second label. Illustrative labels include, e.g., fluorophore, radioactive moiety, enzyme, biotin/avidin label, chromophore, chemiluminescent label, or the like. Any suitable detectable label as is known in the art can be used. For example, the detectable label can be a radioactive label (such as $^{3}H$, $^{125}I$, $^{35}S$, $^{14}C$, $^{32}P$, and $^{33}P$), an enzymatic label (e.g., horseradish peroxidase, alkaline phosphatase, alkaline peroxidase, glucose 6-phosphate dehydrogenase, and the like), a chemiluminescent label (e.g., acridinium esters, thioesters, or sulfonamides; luminol, isoluminol, phenanthridinium esters, and the like), one or more chromophores, e.g., one or more dyes which emit light in the ultraviolet or visible region, phosphors, fluorescers, fluorophores (e.g., fluorescent proteins (green fluorescent protein, yellow fluorescent protein, red fluorescent protein, cyan fluorescent protein); phycobilins (phycoerythrin, R-Phycoerythrin, B-Phycoerythrin); Xanthene derivatives (fluorescein, rhodamine, Oregon green, eosin, Texas red); cyanine derivatives (cyanine, Cy dyes, indocarbocyanine, oxacarbocyanine, thiacarbocyanine, merocyanine); naphthalene derivatives (dansyl and prodan derivatives); coumarin derivatives; oxadiazole derivatives (pyridyloxazole, nitrobenzoxadiazole, benzoxadiazole); Pyrene derivatives (cascade blue); oxazine derivatives (Nile red, Nile blue, cresyl violet, oxazine 170); acridine derivatives (proflavin, acridine orange, acridine yellow); arylmethine derivatives (auramine, crystal violet, malachite green); tetrapyrrole derivatives (porphin, phtalocyanine, bilirubin)), luminophores, chemiluminescers, a fluorescent label (e.g., fluorescein (e.g., 5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, and the like)), rhodamine, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

In varying embodiments, the first label or the second label is a phycobilin (e.g., phycoerythrin, R-Phycoerythrin, B-Phycoerythrin). R-Phycoerythrin, or PE, are useful as a fluorescence-based indicator for labeling analyte-binding molecules or other molecules in a variety of applications. R-Phycoerythrin absorbs strongly at about 566 nm with secondary peaks at 496 and 545 nm and emits strongly at 575 nm. R-Phycoerythrin is among the brightest fluorescent dyes ever identified. See, for example, Phycoerythrin —Wikipedia, the free encyclopedia, on the internet at en.wikipedia.org/wiki/Phycoerythrin and R-PHYCOERYTHRIN (PB31), ProZyme Inc., Hayward, Calif., both of which are incorporated herein by reference.

In embodiments where the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution.

The first and second labels or reporter molecules can be any signal generating molecules (e.g., as described above and herein), as long as they can be distinguished from each other. In varying embodiments, they can be independently fluorophores or chemiluminescent probes. In varying embodiments, the can be distinguished by spectral difference, lifetime difference, sequential triggering or other distinguishing properties.

In some embodiments, the kit can include reagents for labeling the analyte-binding molecules or reagents for detecting the analyte-binding molecules (e.g., detection analyte-binding molecules) and/or for labeling the analytes or reagents for detecting the analyte. The analyte-binding molecules, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the assay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

In a particular embodiment, the kits comprise a tracer analyte comprising a first label, a capture analyte-binding molecule, and a detection analyte-binding molecule comprising a second label, wherein the capture analyte-binding molecule and the detection analyte-binding molecule can concurrently bind to the tracer analyte.

6. Assay Formats

The present disclosure provides a method for determining the presence, amount or concentration of analyte (or fragments thereof) in a test sample. Any suitable assay as is known in the art can be used in the method. Examples include, but are not limited to, assay, such as sandwich assay (e.g., including radioisotope detection (radioimmunoassay (RIA)) and enzyme detection (enzyme assay (EIA) or enzyme-linked immunosorbent assay (ELISA) (e.g., Quantikine ELISA assays, R&D Systems, Minneapolis, Minn.)), and homogeneous chemiluminescent assay, etc. In a SELDI-based assay, a capture reagent (e.g., one or more analyte-binding-molecules that specifically bind analyte, is attached to the surface of a mass spectrometry probe, such as a pre-activated protein chip array. A chemiluminescent microparticle assay, in particular one employing the ARCHITECT® automated analyzer (Abbott Laboratories, Abbott Park, Ill.), is an example of a useful assay. Another example of a useful assay is as carried out on an Abbott Point of Care instrument (i-STAT®, Abbott Laboratories). Still another example of a useful assay is one performed on suitable solid support (e.g., microtiter plate) using, for example, a fluorescence microscope.

Methods well-known in the art for collecting, handling and processing urine, blood, serum and plasma, and other body fluids, are used in the practice of the present disclosure, for instance, when the analyte-binding molecules according to the present disclosure are employed as immunodiagnostic reagents, and/or in a kit for assay of analyte. The test sample can comprise further moieties in addition to the analyte, other analytes of interest, such as e.g., proteins, peptides, polypeptides, oligonucleotides or polynucleotides generally, as well as more specifically, e.g., antibodies, antigens, haptens, hormones, drugs, enzymes, or receptors, along with the illustrative analytes described herein and any other analyte of interest. For example, the sample can be a whole blood sample obtained from a subject. It can be necessary or desired that a test sample, particularly whole blood, be treated prior to assay as described herein, e.g., with a pretreatment reagent. Even in cases where pretreatment is not necessary (for example, most urine samples), pretreatment optionally can be done for mere convenience (e.g., as part of a regimen on a commercial platform). Preferably, the test sample is serum.

The pretreatment reagent can be any reagent appropriate for use with the assay and kits described herein. Sackrison et al., for example, discloses lowering the pH of the sample to 5.5 or less to dissociate analyte from analyte-binding proteins (see, e.g., U.S. Pat. App. Pub. No. 2004/0132104). The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S Provisional Pat. App. 60/878,017, filed Dec. 29, 2006, and U.S. Pat. App. Pub. No. 2008/0020401 (incorporated by reference in its entirety for its teachings regarding pretreatment). The pretreatment reagent can be a heterogeneous agent or a homogeneous agent.

With use of a heterogeneous pretreatment reagent, the pretreatment reagent optionally precipitates antibodies present in the sample. Such a pretreatment step comprises removing any antibodies by separating from the precipitated antibodies the supernatant of the mixture formed by the addition of the pretreatment agent to the sample. In such an assay, the supernatant of the mixture absent any binding protein is used in the assay, proceeding directly to the capture step.

With use of a homogeneous pretreatment reagent there is no such separation step. The entire mixture of test sample and pretreatment reagent are contacted with a labeled analyte-binding molecule specific for analyte (or fragments thereof), such as a labeled antibody or antigenically reactive fragment thereof that specifically binds analyte. The pretreatment reagent employed for such an assay typically is diluted in the pretreated test sample mixture, either before or during capture by the first analyte-binding molecule. Despite such dilution, a certain amount of the pretreatment reagent (for example, 5 M methanol and/or 0.6 M ethylene glycol) is still present (or remains) in the test sample mixture during capture.

In a heterogeneous format, after the test sample is obtained from a subject, a first mixture is prepared. The mixture contains the test sample being assessed for analyte (or fragments thereof) and a first or capture analyte-binding molecule (e.g., antibody or antigenically active fragment thereof), wherein the analyte-binding molecule and any analyte contained in the test sample or tracer analyte form an analyte-binding molecule-analyte complex or analyte-binding molecule-tracer analyte complex. In varying embodiments, the first or capture analyte-binding molecule can be an antibody (or fragment thereof) that specifically binds analyte, e.g., antibodies described herein, or other commercially available antibodies. The test sample and the tracer analyte should be introduced to other analyte-binding molecules at the same time. In varying embodiments, the first or capture analyte-binding molecule is immobilized on a solid support. The solid support used in the assay (for a first analyte-binding molecule) can be any solid support known in the art, such as, but not limited to, an electrode, a magnetic particle, a microparticle, a bead, a test tube, a microtiter plate, a cuvette, a membrane, a scaffolding molecule, a film, a filter paper, a disc and a chip.

After the mixture containing the first or capture analyte-binding molecule-analyte complexes are formed, any unbound analyte is removed from the complex using any technique known in the art. For example, the unbound analyte can be removed by washing. Desirably, however, the analyte-binding molecules are present in excess of any analyte present in the test sample, such that all analyte that is present in the test sample is bound by the analyte-binding molecules.

After any unbound analyte is removed, a second or detection analyte-binding molecule is added to the mixture to form a first or capture analyte-binding-molecule-analyte-second or detection analyte-binding molecule complex. In varying embodiments, the detection analyte-binding molecule is an antibody (or fragment thereof) that specifically binds analyte. Generally, the detection analyte-binding molecules are labeled with or contain a detectable label as described herein.

Analyte assays generally can be conducted using any format known in the art, such as, but not limited to, a sandwich format, as further described in U.S. Patent Application Publication No. US 2009-0269777, which was published on Oct. 29, 2009, and which is hereby incorporated by reference. Specifically, in one format an analyte-binding molecule (e.g., an antibody or antigenically reactive fragment thereof) that specifically binds to analyte is employed to determine the total amount of analyte (or fragments thereof) in a sample. More specifically, the analyte-binding molecule (e.g., an antibody or antigenically reactive fragment thereof) bind to analyte forming an immune complex, which is referred to as a "sandwich," with each. Generally, the analyte-binding molecule (e.g., an antibody or antigenically reactive fragment thereof) used to capture analyte (or fragments thereof) in the test sample is referred to as a "capture agent", e.g., a "capture antibody" in the case of an antibody. The analyte-binding molecule (e.g., an antibody or antigenically reactive fragment thereof) used to bind a detectable and quantifiable label to the sandwich is referred to as a "detection agent", e.g., a "detection antibody" in the case of an antibody, or a "conjugate."

Generally, a sample being tested for (for example, suspected of containing) analyte (or fragments thereof) can be contacted with at least one capture agent (e.g., analyte-binding molecule (e.g., capture antibody or antigenically reactive fragment thereof)) and at least one detection agent (e.g., detection analyte-binding molecule (e.g., an antibody or antigenically reactive fragment thereof)) either simultaneously or sequentially and in either order. For example, the test sample can be first contacted with at least one capture agent and then (sequentially) with at least one detection agent. Alternatively, the test sample can be first contacted with at least one detection agent and then (sequentially) with at least one capture agent. In yet another alternative, the test sample can be contacted simultaneously with a capture agent and a detection agent.

In the sandwich assay format, a sample suspected of containing analyte (or fragments thereof) is first brought into contact with an at least one capture agent under conditions that allow the formation of a capture agent/analyte complex. If more than one capture agent is used, a multiple capture agent/analyte complex is formed.

Optionally, prior to contacting the test sample with the at least one capture agent, the at least one capture agent can be bound to a substrate to facilitate separation of the capture agent/analyte complex. The substrate to which the capture agent is bound can be any suitable solid support or solid support that facilitates separation of the capture agent/analyte complex from the sample, as described above and herein.

After the test sample being assayed for analyte (or fragments thereof) is brought into contact with at least one capture agent, the mixture is incubated in order to allow for the formation of a capture agent/analyte complex. If the test sample is brought into contact with more than one capture agent, then multiple capture agent/analyte complexes are formed. The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes. The assay described herein can be conducted in one-step (meaning the test sample, at least one capture agent and at least one detection agent are all added sequentially or simultaneously to a reaction vessel) or in more than one-step, such as two steps, three steps, etc.

After formation of the capture agent/analyte complex, the complexes are then contacted with at least one detection agent (under conditions which allow for the formation of a capture agent/analyte/detection agent complex). If the capture agent/analyte complex are contacted with more than one detection agent, then multiple capture agent/analyte/detection agent complexes are formed. As with the capture agent, when the at least one detection agent is brought into contact with the capture agent/analyte complex, a period of incubation under conditions similar to those described above is required for the formation of the capture agent/analyte/detection agent complex(es). Preferably, at least one detection agent contains a detectable label. The detectable label can be bound to the at least one detection agent prior to, simultaneously with, or after the formation of the capture agent/analyte/detection agent complex(es). Any detectable label known in the art can be used (see discussion above, including Polak and Van Noorden (1997) and Haugland (1996)).

The detectable label can be bound to the detection agent either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to a detection agent are known in the art. Additionally, many detectable labels can be purchased or synthesized that already contain end groups that facilitate the coupling of the detectable label to the analyte-binding molecule, such as CPSP-Acridinium Ester (i.e., 9-[N-tosyl-N-(3-carboxypropyl)]-10-(3-sulfopropyl)acridinium carboxamide) or SPSP-Acridinium Ester (i.e., N10-(3-sulfopropyl)-N-(3-sulfopropyl)-acridinium-9-carboxamide).

The capture agent/analyte/detection agent complex(es) can be, but do not have to be, separated from the remainder of the test sample prior to quantification of the label. For example, if the at least one capture agent is bound to a solid support, such as a well or a bead, separation can be accomplished by removing the fluid (of the test sample) from contact with the solid support. Alternatively, if the at least one capture agent is bound to a solid support, it can be simultaneously contacted with the test sample and the at least one detection agent to form a capture agent/analyte/detection agent complex(es), followed by removal of the test sample from contact with the solid support. If the at least one capture agent is not bound to a solid support, then the capture agent/analyte/detection agent complex(es) do not have to be removed from the test sample for quantification of the amount of the label. When the assay does not includes a separation of bound from unbound sample analyte it is considered 'one-step' assay. When the assay does include a separation of bound from unbound sample analyte it generally is considered a 'two-step assay' (or delayed one-step assay, depending on how the separation is carried out).

After formation of the labeled capture agent/analyte/detection agent complex(es), the amount of label in the complex(es) is quantified using techniques known in the art. The signal (e.g., color, light, radioactivity, reactive oxygen species) that is generated can be detected using routine techniques known to those skilled in the art. Based on the intensity of the signal generated, the amount of analyte in the sample can be quantified. Specifically, the amount of analyte in the sample is proportional to the intensity of the signal generated. The amounts of analyte present can be quantified by comparing the amount of signal to a reference standard.

For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc.

In varying embodiments, the methods employ microparticle solid supports and are performed using automated or semi-automated systems. Imaging systems suitable for use in the methods described herein can be any system capable of obtaining images such that individual microparticles can be resolved. Imaging devices suitable for use with the method described herein include, but are not limited to, light microscopes, fluorescence imaging scanners, and the like. Such use of imaging systems are described, e.g., in U.S. Patent Publ. 2012-0308997, incorporated by reference for its teachings regarding same. Image file types that are suitable for use with the method described herein include, but are not limited to, JPEG/JFIF, GIF, BMP, TIFF, and FITS. Image file formats are described at Image file formats—Wikipedia, the free encyclopedia, which is accessible by means of Hypertext Transfer Protocol at the website en.wikipedia.org/wiki/image_file_formats, incorporated herein by reference, and FITS is described at FITS—Wikipedia, the free encyclopedia, which is accessible by means of Hypertext Transfer Protocol at the website en.wikipedia.org/wiki/FITS, incorporated herein by reference.

Duration of exposure during acquisition of the image is not critical. Exposure times suitable for use with the method described herein can be any exposure time that provides sufficient resolution for discerning relevant details of the image.

The selection of the region of interest is important. Through the use of a suitable computer program, the locations of individual microparticles are determined by means of contrast or some alternative criteria. The pixels associated with the microparticles or other solid support can be deemed a region of interest. In order to obtain a meaningful value of concentration of an analyte in a sample, typically at least about 100 microparticles, e.g., at least about 200 microparticles are located in an image. Commercially available computer programs suitable for use in the method described herein include, but are not limited to, those programs having the trademarks "SLIDEBOOK" (Intelligent Imaging Innovations, Inc., Denver, Colo.; on the internet at slidebook.com) and "METAMORPH" (Molecular Devices, LLC, Sunnyvale, Calif.) or software in the public domain, such as, for example, ImageJ (on the internet at rsbweb.nih.gov/ij/).

In performing one form of the method, a commercially available fluorescence microscope, e.g., an epifluorescence microscope, can be used to image the complexes through a transparent surface upon which they are supported. A standard epifluorescence microscope, a confocal or TIRF (total internal reflection fluorescence) microscope can be used. In varying embodiments, a TIRF microscope is used because this type of microscope has better z-plane resolution, which can eliminate signals from above the focal plane where the microparticles are positioned, thereby lowering the background signal. A representative example of such a microscope is a motorized inverted fluorescence microscope (e.g., OLYMPUS "IX81"; on the internet at olympusamerica.com/) coupled with a high resolution CCD camera (e.g., Hamamatsu Model C4742-80-12AG; on the internet at learn.hamamatsu.com/products). Other comparable microscopes and cameras that find use are commercially available.

In this basic form of the method, a single-color approach can be used to provide greater sensitivity than a conventional assay employing a light signal from the total volume of a reaction mixture. This greater sensitivity can be evidenced by a plot of a linear function having a greater slope at lower concentrations relative to that of a linear plot employed as a calibration curve in a conventional assay.

Microparticles bearing capture analyte-binding molecules, detection analyte-binding molecules attached to fluorophores, and a sample suspected of containing an analyte are combined under appropriate conditions to carry out an assay. After the assay is carried out, any fluorescent light signal that does not emanate from a complex comprising a microparticle attached to a capture analyte-binding molecule, an analyte, and a conjugate comprising a detection analyte-binding molecule attached to a fluorophore is omitted. Then, the complexes remaining are further qualified based on fluorescence emitted by the fluorophore of the conjugate. This latter step omits any sections on the surface of the microparticle that do not meet selection criteria. Based on a statistical parameter, such as, for example, standard deviation, a typical example of a selection criterion is that the microparticles to be used for measurement have a substantially homogeneous coating, which essentially eliminates excessive aggregation of conjugates, which can result from a high degree of non-specific binding. In general, selection criteria vary, depending upon the particular assay. One of ordinary skill in the art of the particular assay should be able to formulate meaningful selection criteria for that particular assay. Finally, the average value of intensity per pixel of the qualified particles is measured in order to compare the intensity to a calibration curve that establishes concentration of the analyte as a function of intensity. The average value of intensity per pixel of the qualified particles can be determined by means of a CCD camera, which is capable of measuring intensity of light. The measurement of intensity is converted to a parameter, which is designated in the units of counts. Each pixel has a number corresponding to the intensity of light measured at that pixel.

In another embodiment, a white light image of the reaction mixture is obtained. The white light image is employed to locate the position of each solid support, e.g., microparticle. A white light image s formed by using the entire electromagnetic spectrum for both illumination and detection. This step is not required, but is useful because it eliminates signals not originating from microparticles. A fluorescence image is then acquired to determine the location and intensity of detection analyte-binding molecules attached to microparticles. The fluorescence image uses a color, e.g., red, green. Counts per pixel are calculated and the average and standard deviation of counts per pixel are recorded. Pixels that have counts greater than or less than, for example, two times the aforementioned standard deviation are omitted from the analysis. The average number of counts per pixel for the pixels remaining is calculated. The quantity of signal measured from the label of the detection analyte-binding molecule determines the concentration of the analyte.

In order to carry out a measurement that will provide a higher degree of sensitivity, a commercially available epifluorescence microscope can be used to image the complexes through a transparent surface upon which they are supported. A representative example of such a microscope is a motorized inverted fluorescence microscope (e.g., OLYMPUS "IX81") coupled with a high resolution CCD camera (e.g., Hamamatsu Model C4742-80-12AG), which are commercially available from numerous sources.

In this higher sensitivity measurement, a dual-color approach is used to provide greater sensitivity than both a conventional assay employing a light signal from the total volume of reaction mixture and a measurement made by the single-color approach described earlier. This greater sensitivity is evidenced by a plot of a linear function having a greater slope at lower concentrations relative to that of a linear plot employed as a calibration curve in a conventional assay or an assay using the single-color approach. For performing the present methods commercially available instrumentation is adapted to add a second detection channel for detecting the first tripartite complex identified by the first label and a second channel for detecting the second tripartite complex identified by the second label. A fluorescence channel is defined with a set of filters comprising an excitation filter and an emission filter, which allows light having a specific wavelength to reach the sample and a signal having a specific wavelength to reach the CCD camera. For example, the fluorophore PE can only be detected in the PE channel and cannot be detected in any other fluorescence channel. Similarly, the fluorophore Cy5 can only be detected in the Cy5 channel and cannot be detected in any other fluorescence channel. Representative automated and semi-automated systems that can be readily adapted to include a second detection channel, include, e.g., ARCHITECT®, AxSYM®, IMx® PRISM®, EIA (bead), Quantum™ II, and Abbott Point of Care (i-STAT®, Abbott Laboratories).

Microparticles bearing capture analyte-binding molecules, detection analyte-binding molecules attached to fluorophores, and a sample suspected of containing an analyte are combined under appropriate conditions to carry out an assay. After the assay is carried out, any fluorescent light signal that does not emanate from a complex comprising microparticle attached to a capture analyte-binding molecule, an analyte, and a conjugate comprising a detection analyte-binding molecule attached to a first fluorophore is omitted. Next, an image of the capture analyte-binding molecule (characterized by a second fluorophore, which is different from the first fluorophore) is obtained. This image omits any pixels corresponding to any microparticles that are not coated with capture analyte-binding molecule in a homogeneous manner. If a microparticle is not uniformly coated, pixels from that part are omitted. Then, the complex is further qualified based on fluorescence emitted by the conjugate. This latter step omits any sections on the complex that do not meet selection criteria. A typical example of a selection criterion is homogeneous coating, which essentially eliminates excessive aggregation of conjugates, which can result from a high degree of non-specific binding. As stated previously, selection criteria vary, depending upon the particular assay. Finally, the average value of intensity per pixel of the qualified particles is measured in order to compare the intensity to a calibration curve that establishes concentration of the analyte.

In another embodiment, a white light image of the sample is obtained. The white light image is employed to determine the location of microparticles. This step is not required, but is useful because it may be desirable to locate the position of each solid support, e.g., microparticle. A first fluorescence image is then acquired to determine the locations of the capture analyte-binding molecules attached to microparticles. The first fluorescence image uses a color, e.g., red, green. A second fluorescence image is acquired to determine the locations of analyte-binding molecules that are present as a component of a conjugate. The second fluorescence image uses a color, e.g., red, green, but the color of the second fluorescent image differs from the color of the first fluorescent image. Pixels derived from both a capture analyte-binding molecule on a microparticle and an analyte-binding molecule on a conjugate are selected for further analysis. Counts per pixel are calculated and the average and standard deviation of counts per pixel are recorded. Pixels that have counts greater than or less than, for example, two times the standard deviation calculated are omitted from the analysis. The average number of counts per pixel for the pixels remaining is calculated. The quantity of signal measured from the label of the detection analyte-binding molecule determines the concentration of the analyte.

7. Adaptation of Kits and Methods for Particular Instruments

The kit (or components thereof), as well as the methods of determining the concentration of analyte in a test sample by an assay as described herein, can be adapted for use in a variety of automated and semi-automated systems (including those wherein the solid support comprises an electrode or a microparticle). The following adaptations are included as merely exemplary. Illustrative automated and semi-automated systems are described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the capture analyte-binding molecule(s) (e.g., capture analyte-binding molecule, e.g., antibody or antigenically active fragments thereof) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection analyte-binding molecule(s) (e.g., detection analyte-binding molecule, e.g., antibody, or antigenically active fragments thereof) such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical assay system that performs sandwich assays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is useful. A microfabricated silicon chip is manufactured with a pair of gold amperometric working electrodes and a silver-silver chloride reference electrode. On one of the working electrodes, polystyrene beads (0.2 mm diameter) with immobilized capture analyte-binding molecule(s) are adhered to a polymer coating of patterned polyvinyl alcohol over the electrode. In the typical I-STAT® assay the other electrode is coated with a reference bead or microparticle coated with anti-human serum albumin, or another protein which does not bind the analyte of interest. This chip is assembled into an I-STAT® cartridge with a fluidics format suitable for assay. On a portion of the wall of the sample-holding chamber of the cartridge there is a layer comprising the detection analyte-binding molecule(s) labeled with alkaline phosphatase (or other label). Within the fluid pouch of the cartridge is an aqueous reagent that includes p-aminophenol phosphate.

In operation, a sample containing analyte is added to the holding chamber of the test cartridge and the cartridge is inserted into the I-STAT® reader. After the detection analyte-binding molecule(s) (e.g., detection analyte-binding molecule, e.g., antibody or antigenically active fragment thereof) has dissolved into the sample, a pump element within the cartridge forces the sample into a conduit containing the chip. Here it is oscillated to promote formation of the sandwich between the capture analyte-binding molecule(s), analyte, and the labeled detection analyte-binding molecule(s). In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte in the sample by means of an embedded algorithm and factory-determined calibration curve.

It further goes without saying that the methods and kits as described herein necessarily encompass other reagents and methods for carrying out the assay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino) ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-STAT® cartridge format, using a nucleic acid sequence linked to the signal or detection analyte-binding molecule as a signal amplifier.

Generally, for use with the present kits and methods, automated and semi-automated systems are adapted to analyze samples using two different channels, a first channel for detecting the first tripartite complex identified by the first label and a second channel for detecting the second tripartite complex identified by the second label.

Generally, the present kits and methods can be employed for any purpose, e.g., for diagnosing, prognosticating, or assessing the efficacy of therapeutic/prophylactic treatment of a patient, among other uses.

EXAMPLES

The following examples serve to illustrate the present disclosure. The examples are not intended to limit the claimed invention in any way.

Example 1

Titration of Neutrophil Gelatinase-Associated Lipocalin (NGAL)

This example demonstrates the functionality and usefulness of employing a single tracer analyte as an internal calibrator using the representative analyte, NGAL.

These studies were done using an antibody produced by the murine hybridoma cell line 1-2322-455 having ATCC Accession No. PTA-8024 (hereafter "mAb2322"), and an antibody produced by murine hybridoma cell line 1-903-430 having ATCC Accession No. PTA-8026 (hereafter "mAb903"). Murine hybridoma cell lines 1-903-430 and 1-2322-455 were each deposited with the American Type Culture Collection (hereinafter referred to as "ATCC"), 10801 University Blvd., Manassas, Va. 20110-2209, on Nov. 21, 2006. Cell line 1-903-430 was assigned ATCC Accession No. PTA-8026. Cell line 1-2322-455 was assigned ATCC Accession No. PTA-8024. Microparticles were coated with anti-NGAL antibody mAb2322. Anti-NGAL murine monoclonal antibodies and recombinant human NGAL were produced and purified as previously published (Olejniczak, E. T., Ruan, Q., Ziemann, R. N., Birkenmeyer, L. G., Saldana, S. C., and Tetin, S. Y. Biopolymers (2010) 93(7):657-67). Microparticles coated with anti-human monoclonal antibody can bind directly to mAb2322.

Anti-NGAL antibody mAb903 was labeled with Cy5 ("Ab-Cy5"). NGAL labeled with Cy3 (NGAL-Cy3) was used as the analyte tracer/internal calibrator. Cy3 and Cy5 are reactive water-soluble fluorescent dyes of the cyanine dye family. Cy3 is fluorescent in the yellow region of the electromagnetic spectrum (approximately 570 nm) but absorbs in the green region of the electromagnetic spectrum (approximately 550 nm). Cy5 is fluorescent in the red region of the electromagnetic spectrum (approximately 650 nm or 670 nm) but absorbs in the orange region of the electromagnetic spectrum (approximately 649 nm). See, for example, "Technical Information on Probes Conjugated to Affinity-Purified Antibodies and to Other Proteins: Cyanine Dyes (Cy2, Cy3, and Cy5)", which is accessible by means of Hypertext Transfer Protocol on the World Wide Web at the website jacsonimmuno.com/technical/f-cy3-5.asp, incorporated herein by reference.

Figure 3:
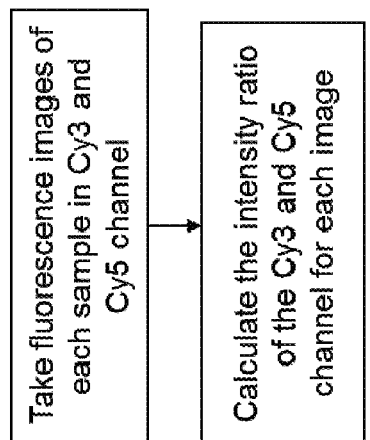
FIG. 3 illustrates a flow chart for neutrophil gelatinase-associated lipocalin (NGAL) titration.

One calibrator and seven samples were prepared as per Table 1, and were processed as depicted in FIG. 3. Generally, the samples having known concentration were treated as if they were test samples.

TABLE 1

| Calibrator ("calibrator") | 40 pM NGAL-Cy3 (100 µL) + 10 µL 0.01% microparticles + 10 µL 16 nM Ab-Cy5 |
|---|---|
| Sample 1 ("s1") | 1 nM NGAL and 40 pM NGAL-Cy3 mixture (100 µL) + 10 µL 0.01% microparticles + 10 µL 16 nM Ab-Cy5 |
| Sample 2 ("s2") | 500 pM NGAL and 40 pM NGAL-Cy3 mixture (100 µL) + 10 µL 0.01% microparticles + 10 µL 16 nM Ab-Cy5 |
| Sample 3 ("s3") | 250 pM NGAL and 40 pM NGAL-Cy3 mixture (100 µL) + 10 µL 0.01% microparticles + 10 µL 16 nM Ab-Cy5 |
| Sample 4 ("s4") | 125 pM NGAL and 40 pM NGAL-Cy3 mixture (100 µL) + 10 µL 0.01% microparticles + 10 µL 16 nM Ab-Cy5 |
| Sample 5 ("s5") | 62 pM NGAL and 40 pM NGAL-Cy3 mixture (100 µL) + 10 µL 0.01% microparticles + 10 µL 16 nM Ab-Cy5 |
| Sample 6 ("s6") | 31 pM NGAL and 40 pM NGAL-Cy3 mixture (100 µL) + 10 µL 0.01% microparticles + 10 µL 16 nM Ab-Cy5 |
| Sample 7 ("s7") | 15 pM NGAL and 40 pM NGAL-Cy3 mixture (100 µL) + 10 µL 0.01% microparticles + 10 µL 16 nM Ab-Cy5 |

Table 2 lists the Cy5/Cy3 intensity ratio for each sample, and the concentration of NGAL (i.e., [analyte]) that was measured using the formula:

$$[\text{analyte}] = \frac{Cy5}{Cy3} \times \frac{[\text{tracer}]}{F} - [\text{Tracer}]$$

where the tracer analyte concentration (i.e., [Tracer]) is 40 pM, the correction factor F is 2.0, and Cy5/Cy3 is the intensity ratio listed in the second column of Table 2.

TABLE 2

| NGAL Sample (pM) | Intensity ratio of Cy5/Cy3 | Measured Total NGAL Concentration | Measured Analyte Concentration (pM) | Standard Deviation |
|---|---|---|---|---|
| 1000 (s1) | 55.3 | 1108.0 | 1068.0 | 9.8 |
| 500 (s2) | 28.1 | 562.1 | 522.1 | 12.8 |
| 250 (s3) | 14.9 | 297.9 | 257.9 | 4.4 |
| 125 (s4) | 8.2 | 164.5 | 124.5 | 1.2 |
| 62.5 (s5) | 5.1 | 101.2 | 61.2 | 1.3 |
| 31.25 (s6) | 3.5 | 69.2 | 29.2 | 1.3 |
| 15.625 (s7) | 2.7 | 54.2 | 14.2 | 0.8 |
| 0 (calibrator) | 2.0 | 40 | 0.0 | 0.6 |

As can be seen from Table 2, there is good agreement between the known (prepared) sample concentration (column 1) and the measured analyte concentration (column 3).

Example 2

NGAL Assay

This example demonstrates an NGAL assay that was performed using ARCHITECT® NGAL assay and calibrator kits (Abbott Laboratories, Abbott Park, Ill.). The NGAL tracer analyte (NGAL-Cy3) and antibody conjugate (mAb903-Cy5) were prepared separately and used along with components of the kit (e.g., NGAL microparticles and NGAL calibrators).

Five of the six NGAL calibrators in the kit (i.e., calibrators at 10, 100, 500, 1000 and 1500 ng/mL) were processed and treated as if they were test samples. The calibrator at 0 ng/mL was used as the diluent for preparing the internal calibrator. The following steps were performed for each of the six.

1. Mix 10 μL of 62.5 ng/ml NGAL-Cy3+10 μL of each NGAL sample+2 μL 800 nM Ab conjugate.
2. Incubate for 5 minutes.
3. Add 2 μL of NGAL 0.1% microparticles.
4. Incubate for 5 minutes.
5. Wash twice with HBS-EP buffer (GE Healthcare, Inc., Catalog Number BR-1001-88; 10 mM HEPES (4-(2-hydroxyethyl)-1-piperazineethanesulfonic acid), 150 mM NaCl, 3 mM EDTA, and 0.005% Tween-20).

After steps 1-5 were done, the fluorescence images of the samples were taken on the microscope.

The fluorescence intensities of the particles in the Cy3 and Cy5 channels were measured for each sample, and the values are listed in columns 2 and 3 of Table 3 below. The ratio of Cy5/Cy3 (column 4) was used to calculate the NGAL analyte concentration (column 6) in each sample using the same formula:

$$[\text{analyte}] = \frac{Cy5}{Cy3} \times \frac{[\text{tracer}]}{F} - [\text{Tracer}]$$

where the [Tracer] is 62.5 ng/mL, F is 0.57, and Cy5/Cy3 is the intensity ratio listed in the fourth column of Table 3.

TABLE 3

| NGAL (ng/mL) | Cy5 intensity | Cy3 intensity | Cy5/Cy3 Or $I_2/I_1$ | SD | Measured NGAL (ng/mL) | SD |
|---|---|---|---|---|---|---|
| 0 (calibrator) | 508 | 895 | 0.57 | 0.01 | 0.00 | 0.18 |
| 10 | 570 | 871 | 0.66 | 0.01 | 9.61 | 0.36 |
| 100 | 1254 | 815 | 1.54 | 0.01 | 106.77 | 0.84 |
| 500 | 3200 | 627 | 5.11 | 0.12 | 500.62 | 27.78 |
| 1000 | 4985 | 501 | 9.95 | 0.12 | 1032.93 | 50.67 |
| 1500 | 6104 | 428 | 14.28 | 0.22 | 1509.88 | 137.82 |

The correlation between the measured NGAL value and the actual NGAL value was 100% (value obtained by plotting the data and fitting to a line; data not shown). These results confirm that only one calibrator, an internal calibrator, is needed to perform assays using the approach described herein. All measured NGAL values were determined with respect to this calibrator.

Figure 4:
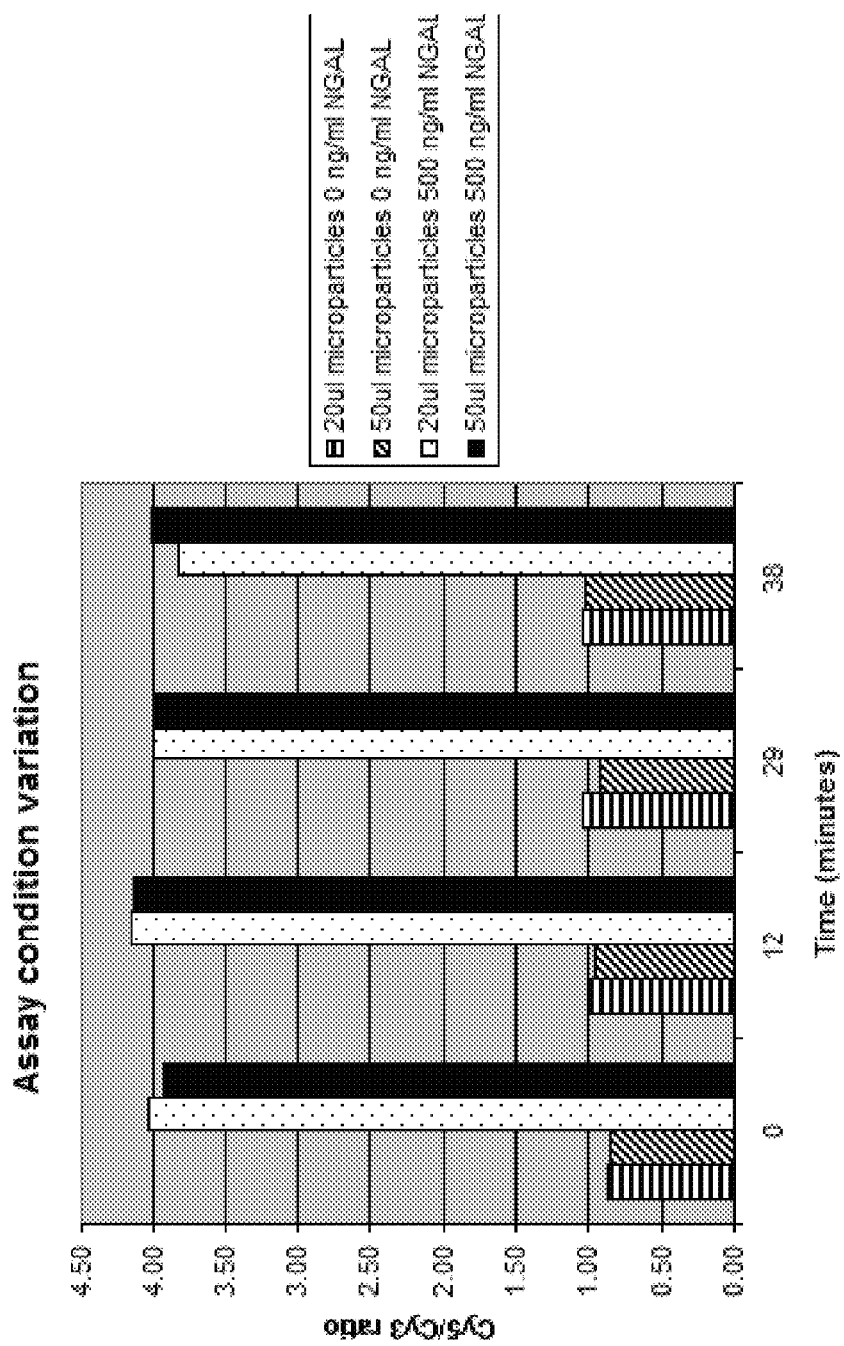
FIG. 4 illustrates internal correction for assay condition variation using a single tracer analyte.

We further varied the NGAL assay conditions, e.g., by using different amounts of microparticles and incubating for different periods of time, as shown in FIG. 4. These results confirmed that the intensity ratio of conjugate or detection antibody (Cy5) and tracer (Cy3) remained constant for a given analyte concentration. This further confirms that the internal calibrator can automatically correct for experimental variations.

It is understood that the examples and embodiments described herein are for illustrative purposes only and that various modifications or changes in light thereof will be suggested to persons skilled in the art and are to be included within the spirit and purview of this application and scope of the appended claims.

The commonly owned, co-pending application U.S. Nonprovisional Application Ser. No. 13/833,655, entitled "ASSAY WITH INCREASED DYNAMIC RANGE," filed on Mar. 15, 2013 is explicitly incorporated by reference in its entirety for its teachings regarding kits and methods for avoiding "hook effect" and increasing assay dynamic range.

All publications, patents, and patent applications cited herein are hereby incorporated by reference in their entirety for all purposes.

What is claimed is:

1. A method of internally calibrating an assay, comprising:
   a) contacting a capture analyte-binding molecule with a predetermined concentration of tracer analyte labeled with a first label and a predetermined concentration of detection analyte-binding molecule labeled with a second label, wherein the capture analyte-binding molecule and the detection analyte-binding molecule concurrently bind to the tracer analyte;
   b) measuring the signal intensities obtained of the first label ($I_1^0$) and of the second label ($I_2^0$);
   c) determining a correction factor (F) as the ratio of the intensity of the second label ($I_2^0$) to the intensity of the first label ($I_1^0$); and
   d) internally calibrating the assay by dividing the predetermined concentration of tracer analyte by the correction factor (F).

2. A method of determining the concentration of analyte in one or more test samples, comprising:
   a) contacting a capture analyte-binding molecule with a predetermined concentration of tracer analyte labeled with a first label and a predetermined concentration of detection analyte-binding molecule labeled with a second label in either the absence or presence of one or more test samples that may comprise test analyte, wherein the capture analyte-binding molecule and the detection analyte-binding molecule concurrently bind to the tracer analyte and, if present, to test analyte in said one or more test samples;
   b) measuring the signal intensities obtained in the absence of said one or more test samples of the first label ($I_1^0$) and the second label ($I_2^0$);
   c) determining a correction factor (F) as the ratio of the intensity of the second label ($I_2^0$) to the intensity of the first label ($I_1^0$);
   d) measuring the signal intensities obtained in the presence of said one or more test samples of the first label ($I_1$) and the second label ($I_2$); and
   e) determining the concentration of test analyte in said one or more test samples by multiplying the ratio of the intensity of the second label ($I_2$) to the intensity of the first label ($I_1$) by the predetermined concentration of tracer analyte divided by the correction factor (F) and subtracting the predetermined concentration of tracer analyte;

$$[\text{analyte}] = \frac{I_2 \times [\text{tracer}]}{I_1 \times F} - [\text{tracer}].$$

3. The method of claim 1, wherein the predetermined concentration of tracer analyte is below saturation of the binding capacity of the capture analyte-binding molecule.

4. The method of claim 2, wherein the predetermined concentration of tracer analyte ranges from less than the expected test analyte concentration to about 5-fold higher than the expected targeted test analyte concentration.

5. The method of claim 1, wherein a two-step assay format is used.

6. The method of claim 5, wherein when a two-step assay format is used, the predetermined concentration of detection analyte-binding molecule equals or exceeds the concentration of analyte and tracer analyte captured in the first step.

7. The method of claim 1, wherein a one-step assay format is used.

8. The method of claim 7, wherein when a one-step assay format is used, the predetermined concentration of detection analyte-binding molecule exceeds the concentration of analyte and tracer analyte.

9. The method of claim 1, wherein the method is performed using an automated or semi-automated system.

10. The method of claim 1, wherein the capture analyte-binding molecule is attached to a solid support.

11. The method of claim 10, wherein the solid support is selected from the group consisting of a particle, a microparticle, a bead, an electrode and a multiwell plate.

12. The method of claim 1, wherein one or both of the capture analyte-binding molecule and/or the detection analyte-binding molecule is an antibody or fragment thereof.

13. The method of claim 1, wherein the first label is a first chromophore and the second label is a second chromophore.

14. The method of claim 13, wherein the first label is a first fluorophore and the second label is a second fluorophore.

15. The method of claim 2, wherein steps b) and d) can be done at the same time, or in any order.

16. The method of claim 2, wherein steps d) and e) are repeated one or more times.

17. The method of claim 2, wherein steps a) through c) are performed only once.

* * * * *